US010258696B2

(12) United States Patent
Mickle et al.

(10) Patent No.: US 10,258,696 B2
(45) Date of Patent: Apr. 16, 2019

(54) BENZOIC ACID, BENZOIC ACID DERIVATIVES AND HETEROARYL CARBOXYLIC ACID CONJUGATES OF HYDROMORPHONE, PRODRUGS, METHODS OF MAKING AND USE THEREOF

(71) Applicant: KemPharm, Inc., Coralville, IA (US)

(72) Inventors: Travis Mickle, Kissimmee, FL (US); Sven Guenther, Coralville, IA (US); Guochen Chi, Coralville, IA (US); Jaroslaw Kanski, Blacksburg, VA (US); Andrea K. Martin, Fincastle, VA (US); Bindu Bera, Blacksburg, VA (US)

(73) Assignee: KemPharm, Inc., Celebration, FL (US)

( * ) Notice: Subject to any disclaimer, the term of this patent is extended or adjusted under 35 U.S.C. 154(b) by 0 days.

(21) Appl. No.: 16/054,575

(22) Filed: Aug. 3, 2018

(65) Prior Publication Data

US 2018/0339056 A1 Nov. 29, 2018

Related U.S. Application Data

(60) Continuation of application No. 15/812,823, filed on Nov. 14, 2017, now Pat. No. 10,064,956, which is a continuation of application No. 15/395,475, filed on Dec. 30, 2016, now Pat. No. 9,849,185, which is a division of application No. 14/336,549, filed on Jul. 21, 2014, now Pat. No. 9,566,343, which is a continuation of application No. 13/660,112, filed on Oct. 25, 2012, now Pat. No. 8,816,083.

(60) Provisional application No. 61/657,201, filed on Jun. 8, 2012, provisional application No. 61/551,600, filed on Oct. 26, 2011.

(51) Int. Cl.
*C07D 489/02* (2006.01)
*A61K 31/485* (2006.01)
*A61K 47/55* (2017.01)
*A61K 47/54* (2017.01)
*A61K 9/00* (2006.01)
*A61K 31/616* (2006.01)
*A61K 31/185* (2006.01)

(52) U.S. Cl.
CPC ............ *A61K 47/55* (2017.08); *A61K 9/0019* (2013.01); *A61K 9/0043* (2013.01); *A61K 9/0053* (2013.01); *A61K 31/185* (2013.01); *A61K 31/485* (2013.01); *A61K 31/616* (2013.01); *A61K 47/542* (2017.08)

(58) Field of Classification Search
CPC .............. A61K 31/485; C07D 489/02
USPC ........................................ 514/282; 546/45
See application file for complete search history.

(56) References Cited

U.S. PATENT DOCUMENTS

| 4,668,685 | A | 5/1987 | Shami |
| 6,150,524 | A | 1/2000 | Hartmann et al. |
| 8,816,083 | B2 * | 8/2014 | Mickle ................ A61K 31/485 |
| | | | 546/44 |
| 9,566,343 | B2 | 2/2017 | Mickle et al. |
| 2003/0022876 | A1 | 1/2003 | Ashton et al. |
| 2011/0002990 | A1 | 1/2011 | Mickle et al. |
| 2011/0002991 | A1 | 1/2011 | Mickle et al. |
| 2011/0015398 | A1 | 1/2011 | Cantrell et al. |

FOREIGN PATENT DOCUMENTS

| CA | 2448665 | 12/2002 |
| EP | 1741426 | 6/2008 |
| WO | 1996022303 | 7/1996 |
| WO | 2001032148 | 5/2001 |
| WO | 2002098427 | 12/2002 |
| WO | 2003011881 | 2/2003 |
| WO | 2005032474 | 4/2005 |
| WO | 2007120864 | 10/2007 |
| WO | 2007140272 | 12/2007 |
| WO | 2008055214 | 5/2008 |
| WO | 2008101202 | 8/2008 |
| WO | 2011002991 | 1/2011 |
| WO | 2011002995 | 1/2011 |
| WO | 2011008636 | 1/2011 |
| WO | 2011009015 | 1/2011 |
| WO | 2012008984 | 1/2012 |
| WO | 2013063204 | 9/2014 |

OTHER PUBLICATIONS

Hussain, Munir A.; Aungst, Bruce J.; Koval, Christopher A.; Shefter, Eli, Improved Buccal Delivery of Opioid Analgesics and Antagonists with Bitterless Prodrugs, Pharmaceutical Research, vol. 5, No. 9, 1988, 615-618.
International Search Report and Written Opinion in PCT/US2012/61813, dated Mar. 8, 2013.
Office Action in U.S. Appl. No. 13/660,112, dated Sep. 11, 2013.
Notice of Allowance in U.S. Appl. No. 13/660,112, dated Apr. 24, 2014.
Colombian Official Action for Appl. No. 14-089.601, dated May 29, 2015.
European Search Report for Appl. No. 12843820.7, dated Jul. 10, 2015.

(Continued)

*Primary Examiner* — Charanjit Aulakh
(74) *Attorney, Agent, or Firm* — McAndrews, Held & Malloy, Ltd.; Robert P. Hoag

(57) ABSTRACT

The presently described technology provides compositions comprising aryl carboxylic acids chemically conjugated to hydromorphone (4,5-α-epoxy-3-hydroxy-17-methyl morphinan-6-one) to form novel prodrugs/compositions of hydromorphone. The hydromorphone prodrugs of the present technology have decreased side effects and decreased potential for abuse compared to unconjugated hydromorphone. The present technology also provides methods of treating patients, pharmaceutical kits and methods of synthesizing conjugates of the present technology.

19 Claims, 23 Drawing Sheets

(56) References Cited

OTHER PUBLICATIONS

Russian Official Decision of Grant for Appl. No. 2014121065, dated Oct. 2, 2015.
Kazakhstan Official Action for Appl No. 2014/1595.1, dated Aug. 21, 2015.
International Search Report and Written Opinion in PCT/US2015/063351, dated May 4, 2016.
Olofson et al., "Selective N-dealkylation of tertiary amines with vinyl chloroformate: An improved synthesis of naloxone", Tetrahedron Letters, vol. 18, No. 18, pp. 1567-1570, 1977.
Koreeda et al., "A new reagent for the selective, high-yield N-dealkylation of tertiary amines: improved syntheses of naltrexone and nalbuphine", The Journal of Organic Chemistry, vol. 49, No. 11, Jun. 1984 (Jun. 1984), pp. 2081-2082.
Andre J-D et al: "O-Demethylation of 1-4,6, Opioid Derivatives with Methane Sulfonic Acid/Methionine: Application to the Synthesis of Naloxone and Analogues", vol. 22, No. 16, 1992, pp. 2313-2327.
Klein et al., "O3-(2-Carbomethoxyallyl) ethers of opioid ligands derived from oxymorphone, naltrexone, etorphine, diprenorphine, norbinaltorphimine, an naltrindole. Unexpected O3-dealkylation in the opioid radioligand displacement assay", Journal of Medicinal and Pharmaceutical Chemistry, vol. 35, No. 24, 1992, pp. 4589-4594.
Koolpe et al., "Diastereomeric 6-Desoxy-6-spiro-alpha-methylene-gamma-butyrolactone Derivatives of Naltrexone and Oxymorphone. Selective Irreversible Inhibition of Naltrexone Binding in an Opioid Receptor Preparation by a Conformationally Restricted Michael Acceptor Ligand", Journal of Medicinal Chemistry, vol. 27, 1984, pp. 1718-1723.
Cheng et al., "N-Cubylmethyl Substituted Morphinoids as Novel Narcotic Antagonists", Bioorganic & Medicinal Chemistry, vol. 4, No. 1, 1996, pp. 73-80.
Machara et al., "Direct Synthesis of Naltrexone by Palladium-Catalyzed N-Demethylation/Acylation of Oxymorphone: The Benefit of C—H Activation and the Intramolecular Acyl Transfer from C-14 Hydroxy", Advanced Synthesis & Catalysis, vol. 354, pp. 2713-2718, 2012.
Beni et al., "Preparation of benzoate esters of morphine and its derivatives", Monatshefte Fur Chemie—Chemical Monthly; An International Journal of Chemistry, vol. 143, No. 10, Jun. 26, 2012 (Jun. 26, 2012), pp. 1431-1440.
Notice of Allowance in U.S. Appl. No. 14/336,549 dated Oct. 7, 2016.

* cited by examiner

Structures of some hydroxybenzoates

Structures of some aminobenzoates

Structures of some aminohydroxybenzoates 4-aminosalicylic acid  3-hydroxyanthranilic acid  3-methoxyanthranilic acid Structures of some heteroaryl carboxylic acids nicotinic acid isonicotinic acid picolinic acid 3-hydroxypicolinic acid 6-hydroxynicotinic acid citrazinic acid 2,6-dihydroxynicotinic acid kynurenic acid xanthurenic acid 6-hydroxy-kynurenic acid 8-methoxykynurenic acid 7,8-dihydroxy-kynurenic acid 7,8-dihydro-7,8-di-hydroxykynurenic acid Structures of some benzylacetates Structures of some cinnamates Figure 8. Oral rat study comparing hydromorphone, 3-aspirin-HM and 3,6-di-aspirin-HM.

Figure 9. Oral rat study comparing hydromorphone and 6-o-salicylate-HM.

Oral PK Curves

Figure 10. Oral rat study comparing hydromorphone and 3-cinnamate-HM.

Figure 11. Oral rat study comparing hydromorphone 6-naproxen-HM.

Figure 12. Oral rat study comparing hydromorphone 3-isoniacin-HM.

Figure 13. Oral rat study comparing hydromorphone and 3-*p*-salicylate-HM.

Figure 14. Oral rat study comparing hydromorphone and 3-fenamate-HM.

Figure 15. Oral rat study comparing hydromorphone, 3-benzoate-HM and 3,6-di-benzoate-HM.

Figure 16. Intranasal rat study comparing hydromorphone and 3,6-di-aspirin-HM.

Figure 17. Intravenous rat study comparing hydromorphone and 3,6-di-aspirin-HM.

Figure 18. Dose escalation in rats

Figure 19. Reduced potency of breakdown products

Figure 20. Motility with 3,6-di-aspirin-HM compared to hydromorphone hydrochloride Figure 21A: Synthesis of 3-aspirin-hydromorphone:

Figure 21B: Synthesis of 3-cinnamate-hydromorphone:

Figure 21C: Synthesis of 3-benzoate-hydromorphone:

Figure 21D: Synthesis of 3,6-di-aspirin-hydromorphone:

Figure 22: Synthesis of 6-salicylate-hydromorphone:

BENZOIC ACID, BENZOIC ACID DERIVATIVES AND HETEROARYL CARBOXYLIC ACID CONJUGATES OF HYDROMORPHONE, PRODRUGS, METHODS OF MAKING AND USE THEREOF

RELATED APPLICATIONS

This application is a continuation of U.S. patent application Ser. No. 15/812,823, which was filed Nov. 14, 2017, which is a continuation of U.S. patent application Ser. No. 15/395,475 which was filed on Dec. 30, 2016, which is a divisional of U.S. patent application Ser. No. 14/336,549 which was filed on Jul. 21, 2014, which is a continuation of U.S. patent application Ser. No. 13/660,112 which was filed on Oct. 25, 2012 which claims the priority of U.S. provisional application Ser. No. 61/657,201, filed Jun. 8, 2012 and U.S. provisional application Ser. No. 61/551,600, filed Oct. 26, 2011, which are incorporated by reference in its entirety.

FEDERALLY SPONSORED RESEARCH OR DEVELOPMENT

[Not Applicable]

BACKGROUND OF THE INVENTION

Opioids are highly effective as analgesics and are commonly prescribed for the treatment of acute and chronic pain. They are also commonly used as antitussives. The opioids, however, also produce euphoria and/or "drug liking effects" and are highly addictive. As a result they are often abused with far reaching social and health related consequences.

Because of the inherent potential for abuse, it is desirable that any pharmaceutical composition containing an opioid agonist be made as abuse-resistant or abuse-deterrent as practical. Illicit users often will attempt to insufflate, inject or otherwise misuse the product in order to achieve a more efficient or immediate effect from the opioid agonist.

Despite their addictive properties and the potential for abuse, morphine-like drugs, particularly, codeine, hydrocodone, hydromorphone and oxycodone have been routinely prescribed as treatment for severe, acute and chronic pain for decades. This is, in part, because there are currently no better alternatives to relieve severe pain that is resistant to other less potent analgesics such as non-steroidal anti-inflammatory drugs (NSAIDS). In this regard, there is a need to decrease the abuse potential of opioid analgesics. Thus far, approaches taken, unfortunately, have not solved the problem.

Hydromorphone (4,5-α-epoxy-3-hydroxy-17-methyl morphinan-6-one) is a hydrogenated ketone of morphine that is used as a centrally acting opioid analgesic and antitussive. Hydromorphone is a semisynthetic narcotic analgesic prepared from morphine that possesses multiple actions qualitatively similar to those of morphine and is used in medicine as an alternative to morphine. It is mainly used for relief of pain and as a narcotic antitussive for cases of dry, painful coughing. Hydromorphone interacts predominantly with the opioid receptors in the central nervous system (CNS). Its analgesic properties are primarily due to agonist activity at the μ-opioid receptor. Hydromorphone is also a partial agonist of the δ-opioid receptor and an agonist of the κ-opioid receptor. Additionally, hydromorphone exhibits antitussive properties by suppressing the cough reflex in the medullary cough center of the brain.

Patients taking opioid analgesics such as hydromorphone for pain and/or cough relief can become unintentionally addicted. As tolerance to the opioids develops, higher amounts of the drug are needed to alleviate the symptoms and generate the sense of wellbeing initially achieved with the prescribed dose. This leads to dose escalation, which, if left unchecked, can lead rapidly to addiction. In some cases patients have become addicted in as little as thirty days.

Opioid induced constipation (OIC) is a common side effect of pain treatment with opioids. It affects approximately 40-90% of the patients who are chronically taking opioid medication. Additionally, patients suffering from OIC may become resistant to laxative treatments. Although the mechanism is not yet fully understood, it is assumed that the binding of agonists to the peripheral μ-opioid receptors in the gastrointestinal (GI) tract is the primary cause of OIC. This opioid receptor activation impairs the coordination of the GI function by the enteric nervous system (ENS) resulting in decreased gut motility by delaying the transit time of fecal content through interference with the normal tone and contractility of the bowels. While the contractions of the circular muscles are increased causing non-propulsive kneading and churning (stasis) and increased fluid absorption, the longitudinal smooth muscle tone is decreased causing reduced forward peristalsis and additional time for desiccating fecal matter. Furthermore, the anal sphincter tone is increased making defecation more difficult. The clinical presentation of these effects typically manifests itself in symptoms of hard/dry stool, straining, incomplete evacuation, bloating and abdominal distention.

BRIEF SUMMARY OF THE INVENTION

The present technology utilizes conjugation of the opioid hydromorphone with certain aryl carboxylic acids to decrease its potential for causing overdose or abuse by requiring the active hydromorphone to be released through enzymatic or metabolic breakdown of the conjugate in vivo. The present technology also provides methods of delivering hydromorphone as conjugates that release the hydromorphone following oral administration while being resistant to abuse by circuitous routes such as intravenous ("shooting") injection and intranasal administration ("snorting").

Advantages of certain embodiments of the hydromorphone prodrugs of the present technology include, but are not limited to, reduced drug abuse potential, reduced or eliminated opioid induced constipation (OIC), reduced risk of chemical or physical manipulation resulting in full dosage of hydromorphone release, reduced patient to patient variability in plasma concentrations compared to free hydromorphone, improved dosage forms through modifications of the physical and chemical properties of the prodrugs and improved side effect profile through reduced conversion of the hydromorphone prodrug to undesirable hydromorphone-3-glucuronide.

In some aspects, the present technology provides an immediate release composition of conjugated hydromorphone that allows delivery of the hydromorphone into the blood system of a human or animal in a therapeutically bioequivalent manner upon oral administration. In at least one aspect, the compositions/formulations of the current technology can lessen common side effects associated with unconjugated hydromorphone and similar compounds. The presently described technology, in at least one aspect, provides a slow/sustained/controlled release composition of conjugated hydromorphone that allows slow/sustained/controlled delivery of the hydromorphone into the blood system of a human or animal within a safe therapeutic window upon, for example, oral administration. At least some compositions/formulations of the current technology can lessen addiction/abuse potential associated with unconjugated hydromorphone and similar compounds.

In additional aspects, the present technology utilizes conjugation of natural non-toxic ligands to hydromorphone to create a new class of prodrugs. The prodrugs of the present technology can be easily recognized by the metabolic systems and hydrolyzed to release the active opioid in a controlled fashion upon oral administration. Other routes of administration render the compounds of the present technology ineffective or less effective, thereby preventing or decreasing drug abuse. Additional methods of drug abuse are also averted due to the physical tampering resistance and prevention or reduction of euphoria upon ingestion of high doses of the prodrugs of the present technology. Depending on the choice of ligand, pharmacokinetic (PK) profiles of hydromorphone liberated from the prodrugs of the present technology can be modulated to optimize blood levels versus time for a specific indication and to improve its safety profile. Additionally, by selecting appropriate ligands, the prodrugs of the present technology can deliver hydromorphone into the systemic circulation without interacting with the opioid receptors in the enteric nervous system thus reducing or preventing opioid induced constipation (OIC).

In another aspect, the present technology provides aryl carboxylic acids chemically attached to hydromorphone to create prodrugs that can release the active opioid. The prodrugs of the present technology do not exhibit significant analgesic activity and by choosing suitable ligands significantly reduce the amounts of hydromorphone released into the systemic circulation when administered intranasally or intravenously. Moreover, the narcotic cannot be "extracted" from the prodrugs of the present technology by simple physical tampering due to the nature of the covalent enol ester and/or phenol ester bond between hydromorphone and the aryl carboxylic acid. This class of compounds, of the present technology, may be viewed as less attractive to potential drug abusers than traditionally formulated drugs and may provide an improved safety profile and reduced side effects.

Additionally, by choosing appropriate ligands, all or most of the inactive prodrugs of the present technology can survive the transit through the gastrointestinal (GI) tract until they are absorbed, thus preventing hydromorphone from interacting with the opioid receptors in the enteric nervous system. This lack of binding to the peripheral opioid receptors can significantly reduce or even prevent opioid induced constipation.

In at least one aspect, the present technology provides at least one prodrug composition comprising at least one conjugate, the conjugate comprising at least one hydromorphone, and at least one aryl carboxylic acid.

In another aspect, the present technology provides at least one hydromorphone prodrug comprising an aryl carboxylic acid chemically bonded to hydromorphone by reacting the carboxylic acid moiety of the aryl carboxylic acid with the C-6 enol tautomer of hydromorphone.

In another aspect, the present technology provides at least one prodrug comprising the at least one hydromorphone chemically bonded to the at least one aryl carboxylic acid by reacting the carboxylic acid moiety of the aryl carboxylic acid with the C-3 hydroxyl of hydromorphone.

In another aspect, the present technology provides a prodrug comprising at least one hydromorphone chemically bonded to at least one aryl carboxylic acid by reacting the carboxylic acid moiety of one aryl carboxylic acid with the C-6 enol tautomer of hydromorphone and reacting at least one aryl carboxylic acid with the C-3 hydroxyl of hydromorphone.

In other aspects, the present technology provides at least one prodrug with at least one aryl carboxylic acid comprising a carboxylic group attached directly to at least one aryl moiety.

In another aspect, the present technology provides at least one prodrug with at least one hydromorphone chemically attached to at least one benzoate of the general formula I:

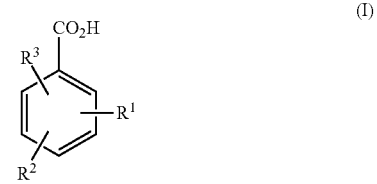

(I)

where $R^1$, $R^2$ and $R^3$ are independently selected from the group consisting of hydrogen, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, phosphonate.

In at least one aspect, the present technology provides a hydromorphone prodrug with at least one aryl carboxylic acid comprising a carboxylic group that is connected by a one-carbon linker to the aryl moiety.

In another aspect, the present technology provides at least one hydromorphone prodrug chemically attached to at least one phenylacetate of the following general formula II:

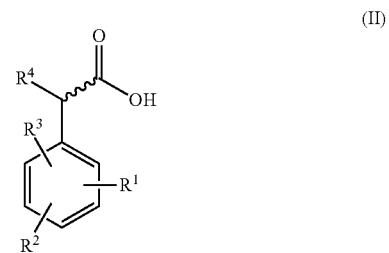

(II)

where $R^1$, $R^2$, $R^3$ and $R^4$ are independently selected from the group consisting of hydrogen, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, phosphonate.

In other aspects, the present technology provides hydromorphone prodrugs containing at least one aryl carboxylic acid comprising a carboxylic group that is connected by a two-carbon linker to the aryl moiety.

In additional aspects, the present technology provides hydromorphone prodrug compositions comprising benzylacetates and cinnamates having the following general formula III or IV or combinations thereof:

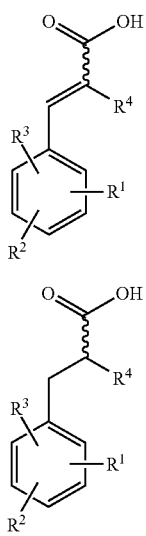

where $R^1$, $R^2$, $R^3$ and $R^4$ are independently selected from the group consisting of hydrogen, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, phosphonate.

In other aspects, the hydromorphone prodrugs of the present technology include at least one aryl carboxylic acid comprising a carboxylic group attached to an aryl moiety ring by an alkyl chain.

In other aspects, the hydromorphone prodrugs of the present technology include at least one aryl carboxylic acid comprising a carboxylic group attached to an aryl moiety ring by an alkenyl chain.

In additional aspects, the hydromorphone prodrugs of the present technology contain at least one aryl carboxylic acid that comprises a carbon chain between the aryl ring and the carboxyl group with one or more side chains.

In additional aspects, the hydromorphone prodrugs of the present technology contain at least one aryl carboxylic acid that comprises one or more functional groups in addition to at least one carboxyl group.

In other aspects, the hydromorphone prodrugs of the present technology contain at least one aryl carboxylic acid that comprises at least one heteroraryl carboxylic acid.

In additional aspects, the present technology provides hydromorphone prodrug compositions comprising heteroraryl carboxylic acid of the following general formula V, VI, VII, VIII, IX, X, XI, XII, or XIII or combinations thereof:

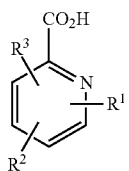

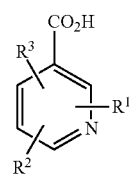
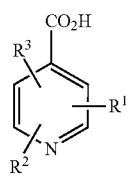
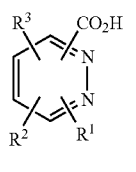
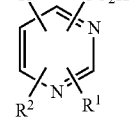
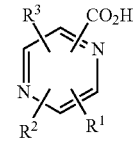
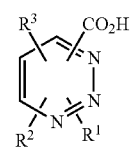
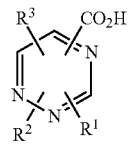
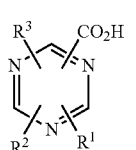
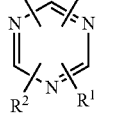

where $R^1$, $R^2$ and $R^3$ are independently selected from the group consisting of hydrogen, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, phosphonate.

In other aspects, the present technology provides at least one hydromorphone prodrug that contains an aryl carboxylic acid comprising a six-membered ring.

In other aspects, the present technology provides at least one hydromorphone prodrug that contains an aryl carboxylic acid comprising only one free carboxylic acid group.

In additional aspects, the present technology provides at least one hydromorphone prodrug that contains an aryl carboxylic acid comprising between 1 to 4 phenyl substituents.

In certain aspects, the present technology provides at least one hydromorphone prodrug conjugate that is a neutral prodrug.

In certain aspects, the present technology provides at least one hydromorphone prodrug conjugate that is a free acid.

In certain aspects, the present technology provides at least one hydromorphone prodrug conjugate that is a free base.

In additional aspects, the present technology provides at least one hydromorphone prodrug conjugate that is a pharmaceutically acceptable anionic or cationic salt form or salt mixtures thereof.

In certain aspects, the hydromorphone prodrug compositions of the present technology are broken down in vivo releasing active hydromorphone and an aryl carboxylic acid or derivatives or metabolites thereof.

In certain aspects, the hydromorphone prodrug compositions of the present technology are administered orally and hydrolyzed in vivo releasing hydromorphone from the prodrug.

In other aspects, the hydromorphone prodrug compositions of the present technology exhibit no or limited pharmacological activity upon administration.

In other aspects, the hydromorphone prodrug compositions of the present technology release hydromorphone in a manner that is similar to free or unmodified hydromorphone upon administration at equimolar dosages.

In additional aspects, the hydromorphone prodrug compositions of the present technology control and limit the release of hydromorphone into the systemic circulation when the prodrug is administered via routes other than oral.

In certain aspects, the hydromorphone prodrug compositions of the present technology release hydromorphone in a controlled or sustained manner upon administration.

In other aspects, the hydromorphone prodrug compositions of the present technology exhibit no or decreased side effects compared to unmodified hydromorphone upon administration at equimolar dosages.

In additional aspects, administration of the hydromorphone prodrug compositions of the present technology results in hydromorphone concentrations in the plasma or blood that are significantly decreased compared to unmodified hydromorphone upon administration at equimolar dosages by intravenous or intranasal routes.

In other aspects, administration of the hydromorphone prodrug compositions of the present technology does not cause or results in reduced euphoria or drug liking effect compared to unmodified hydromorphone upon intranasal or intravenous administration at equimolar dosages.

In some aspects, administration of the hydromorphone prodrug compositions of the present technology does not result in a rapid hydromorphone concentration spike ($C_{max}$) in the blood or plasma upon oral administration.

In other aspects, administration of the hydromorphone prodrug compositions of the present technology results in a delayed $T_{max}$ compared to unmodified hydromorphone when administered orally at equimolar dosages.

In additional aspects, administration of the hydromorphone prodrug compositions of the present technology results in a lower $C_{max}$ value compared to unmodified hydromorphone when administered orally at equimolar dosages.

In further aspects, physical manipulation of the hydromorphone prodrug compositions of the present technology does not result in the liberation of free hydromorphone.

In other aspects, the hydromorphone prodrug compositions of the present technology exhibit resistance to certain chemical manipulations intended to liberate free hydromorphone.

In other aspects, administration of the hydromorphone prodrug compositions of the present technology does not cause or results in insignificant activity at μ-opioid receptors.

In other aspects, the hydromorphone prodrug compositions of the present technology are not or are limitedly subjected to enzymatic hydrolysis until absorbed in the gut.

In further aspects, the hydromorphone prodrug compositions of the present technology exhibit decreased conversion to hydromorphone-3-glucuronide (H3G) compared to unmodified hydromorphone when administered orally at equimolar dosages.

In other aspects, the hydromorphone prodrug compositions of the present technology prevent or decrease opioid induced constipation (OIC) compared to unmodified hydromorphone when administered orally at equimolar dosages.

In other aspects, the hydromorphone prodrug compositions of the present technology comprise additional active pharmaceutical ingredients (APIs), including, for example, ibuprofen, acetaminophen, or aspirin.

In certain aspects, the hydromorphone prodrug compositions of the present technology may be 3-aspirin-hydromorphone, 3,6-di-aspirin-hydromorphone, 6-o-salicylate-hydromorphone, 3-cinnamate-hydromorphone, 6-naproxen-hydromorphone, 3-isoniacin-hydromorphone, 3-p-salicylic-hydromorphone, 3-fenamate-hydromorphone, 3-benzoate-hydromorphone, and 3,6-di-benzoate-hydromorphone.

In other aspects, the hydromorphone prodrug compositions of the present technology are in an oral dosage form. In some aspects, the oral dosage forms of the present technology are solid dosage forms. In additional aspects, the excipients of the present technology are antiadherents, binders, coatings, disintegrants, fillers, flavors, colors, glidants, lubricants, preservatives, sorbents and sweeteners.

In additional aspects, the hydromorphone prodrug compositions of the present technology are provided as tablets, capsules, softgel capsules, modified release capsules, extended release tablets, controlled release capsules, suppositories, powders for injection, oral liquids, cough syrups, transdermal film, oral thin film, slurry or injections.

In certain aspects, the hydromorphone prodrug compositions of the present technology are provided at oral dosage strengths that are equimolar to from about 0.1 mg to about 200 mg of unmodified hydromorphone.

In other aspects, the present technology provides a method of treating a patient in need of an analgesic effect by administering an amount of at least one hydromorphone prodrug composition of the present technology that is therapeutically equivalent to an effective amount of unconjugated hydromorphone.

In further aspects, the present technology provides a method of synthesizing the hydromorphone prodrug compositions of the present technology.

In other aspects, the present technology provides a method of treating a patient in need of an analgesic effect by administering an amount of 3-aspirin-hydromorphone, 3,6-di-aspirin-hydromorphone, 6-salicylate-hydromorphone, 3-cinnamate-hydromorphone, or 3-benzoate-hydromorphone that is therapeutically equivalent to an effective amount of unconjugated hydromorphone.

In additional aspects, the present technology provides a pharmaceutical kit containing a specified amount of individual doses containing an amount of at least one conjugate that is therapeutically equivalent to an effective amount of unconjugated hydromorphone wherein the at least one conjugate comprises at least one hydromorphone and at least one aryl carboxylic acid.

DETAILED DESCRIPTION OF THE INVENTION

Composition

Figure 1A:
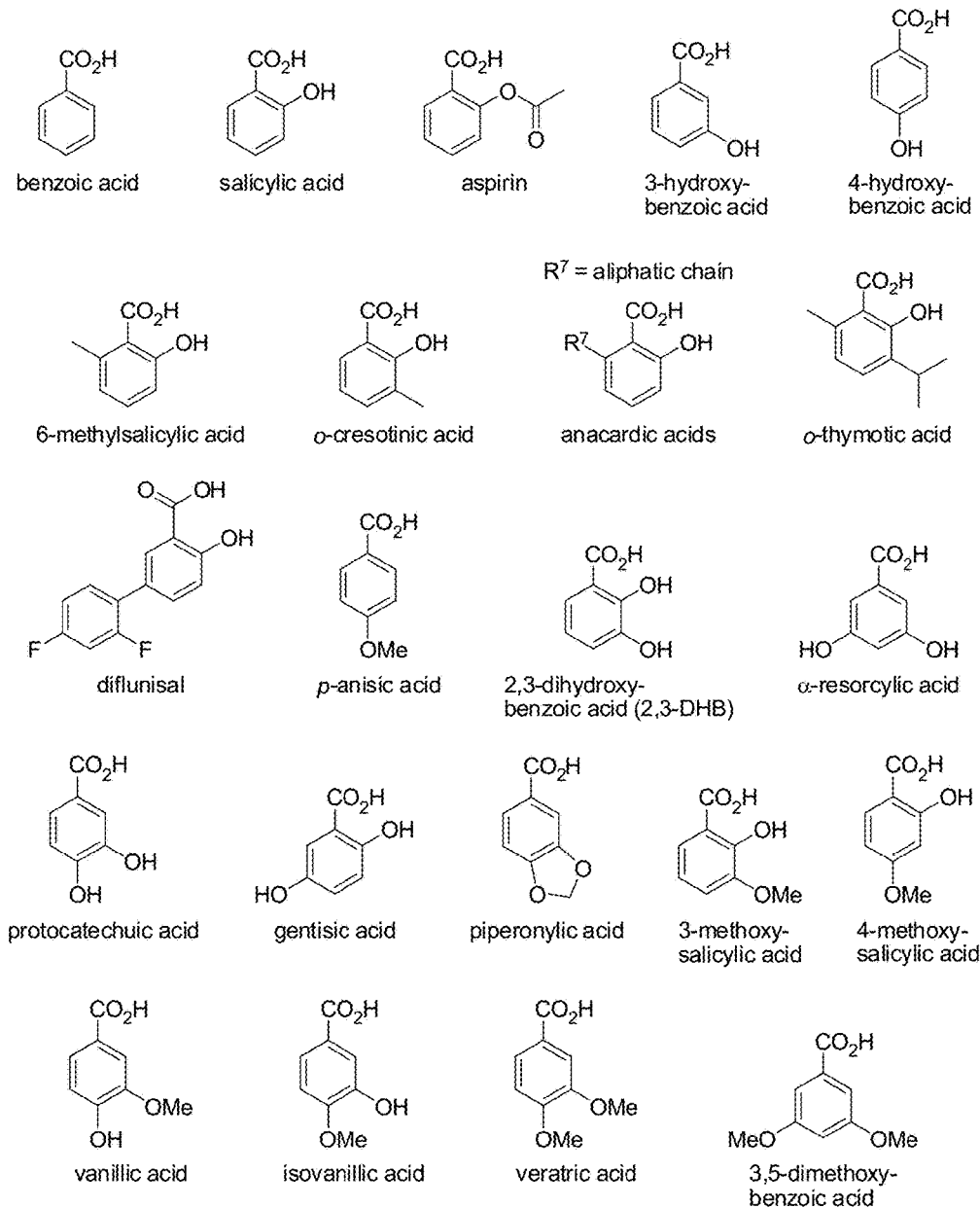
FIGS. 1A and 1B. Example chemical structures of some hydroxybenzoates for use in the making of the hydromorphone prodrug compositions of the present technology.
Figure 1B:
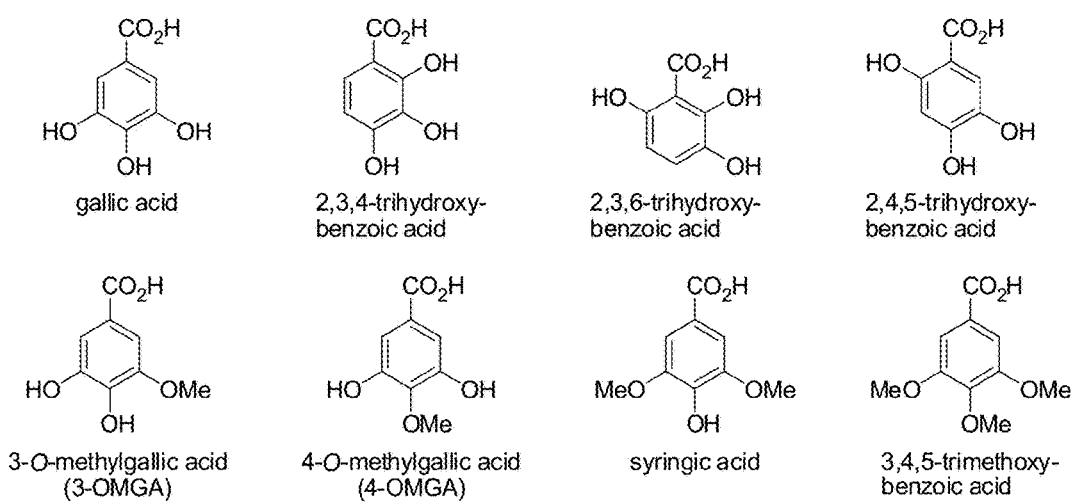
Figure 2:
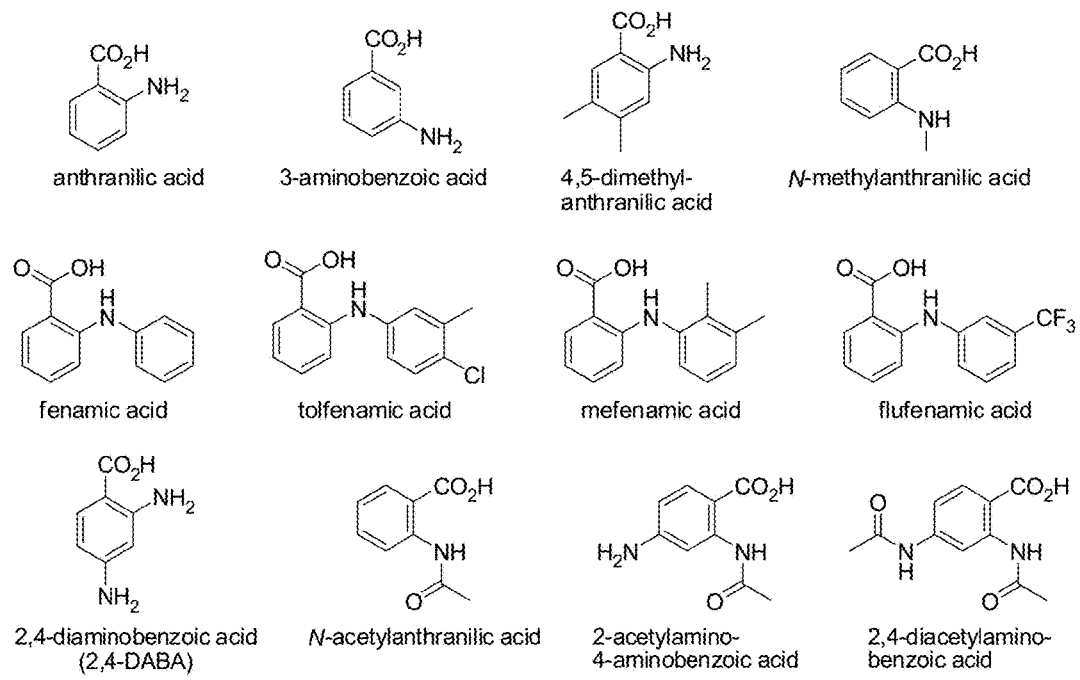
FIG. 2. Example chemical structures of some aminobenzoates for use in the making of the hydromorphone prodrug compositions of the present technology.
Figure 3:
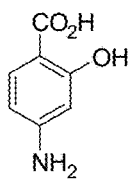
FIG. 3. Example chemical structures of some aminohydroxybenzoates for use in the making of the hydromorphone prodrug compositions of the present technology.
Figure 3:
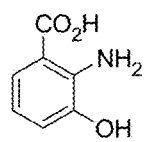
Figure 3:
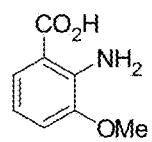

The present technology provides compositions comprising aryl carboxylic acids that are chemically conjugated to hydromorphone (4,5-☐-epoxy-3-hydroxy-17-methylmorphinan-6-one) to form novel prodrugs and compositions of hydromorphone. In some embodiments, the chemical bond between these two moieties can be established by reacting the carboxylic acid function of an aryl carboxylic acid with one of the following functional groups of hydromorphone:

(a) C-6 enol tautomer of hydromorphone
(b) C-3 hydroxyl of hydromorphone,
(c) or both C-3 hydroxyl and C-6 enol tautomer hydromorphone.

The use of "opioid" is meant to include any drug that activates the opioid receptors found in the brain, spinal cord and gut. There are four broad classes of opioids: naturally occurring opium alkaloids, such as morphine (the prototypical opioid) codeine, and thebaine; endogenous opioid peptides, such as endorphins; semi-synthetics such as heroine, oxycodone and hydrocodone that are produced by modifying natural opium alkaloids (opiates) and have similar chemical structures; and pure synthetics such as fentanyl and methadone that are not produced from opium and may have very different chemical structures than the opium alkaloids. Additional examples of opioids are hydromorphone, oxymorphone, methadone, levorphanol, dihydrocodeine, meperidine, diphenoxylate, sufentanil, alfentanil, propoxyphene, pentazocine, nalbuphine, butorphanol, buprenorphine, meptazinol, dezocine, and pharmaceutically acceptable salts thereof.

The use of "therapeutically equivalent" is meant to describe drug products that are pharmaceutical equivalents and can be expected to have the same clinical effect when administered to patients under the conditions specified in the label.

The use of "bioequivalent" is meant to describe pharmaceutical equivalent or pharmaceutical alternative products that display comparable bioavailability (i.e., systemic plasma concentrations of hydromorphone) when studied under similar experimental conditions.

The use of "hydromorphone" is meant to include a semisynthetic narcotic analgesic that possesses multiple actions qualitatively similar to those of morphine and is used in medicine as an alternative to morphine. It is mainly used for relief of pain and as a narcotic antitussive for cases of dry, painful coughing. Trade names include Dilaudid®, Exalgo®, Hydrostat®, and Palladone® (extended release). Other pharmaceutically acceptable salt forms of hydromorphone are also encompassed by certain embodiments of the present technology. The chemical structure of hydromorphone is:

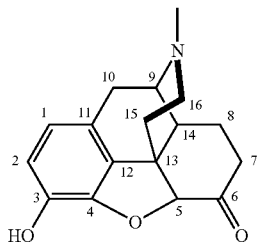

Aryl carboxylic acids of the present technology can be grouped into various categories and subcategories. In certain embodiments, the carboxyl group can be attached directly to the aromatic ring or be separated by an alkyl or alkenyl chain. In other embodiments of the present technology, the chain length of the alkyl or alkenyl group should not exceed two unbranched carbons, but is not limited in numbers of atoms on potential side chains or additional functional groups.

In other embodiments, the present technology includes both carbon only aryl groups and aryl groups with heteroatoms (heteroaryl). The aryl or heteroaryl group of certain embodiments of the present technology, which is connected directly or through an alkyl or alkenyl chain to the carboxyl function, can be a 6-membered ring and contain no, one, or more than one heteroatom. Additional substituted or unsubstituted aromatic or aliphatic rings may be fused to this 6-membered aryl or heteroaryl moiety in certain embodiments of the present technology.

In some embodiments of the present technology, the aryl carboxylic acids may have one or more free carboxylic acid groups and the total number of phenyl substituents on the 6-membered ring can be four or less.

Depending on the individual aryl carboxylic acid that is connected to hydromorphone, the prodrug of the present technology can take on a neutral, free acid, free base, or various pharmaceutically acceptable anionic or cationic salt forms or salt mixtures with any ratio between positive and negative components.

In certain embodiments, salt forms of the prodrugs of the present technology include, but are not limited to: acetate, l-aspartate, besylate, bicarbonate, carbonate, d-camsylate, l-camsylate, citrate, edisylate, formate, fumarate, gluconate, hydrobromide/bromide, hydrochloride/chloride, d-lactate, l-lactate, d,l-lactate, d,l-malate, l-malate, d-malate, mesylate, pamoate, phosphate, succinate, sulfate, bisulfate, d-tartrate, l-tartrate, d,l-tartrate, meso-tartrate, benzoate, gluceptate, d-glucuronate, hybenzate, isethionate, malonate, methylsufate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutarate, glycerophosphate, heptanoate (enanthate), hydroxybenzoate, hippurate, phenylpropionate, iodide, xinafoate, lactobionate, laurate, maleate, mandelate, methanesufonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, and tromethamine.

The prodrugs of certain embodiments of the present technology are designed to be broken down in vivo either enzymatically or otherwise thus releasing the active hydromorphone and the respective aryl carboxylic acid(s) or metabolites thereof. The aryl carboxylic acids of the present technology should be non-toxic at the given dosing levels and are preferably known drugs, natural products, metabolites, or GRAS (Generally Recognized As Safe) compounds (e.g., preservatives, dyes, flavors, etc.) or non-toxic mimetics thereof.

In some embodiments, the aryl carboxylic acids of the present technology comprise a carboxylic group that is attached directly to the aryl moiety. These aryl carboxylic acids can be divided into two subcategories: benzoates and heteroaryl carboxylic acids.

Benzoates

Benzoates of certain embodiments of the present technology include aminobenzoates (e.g., anthranilic acid analogs such as fenamates) and hydroxybenzoates (e.g., salicylic acid analogs). The general chemical structure of the benzoates of the present technology is represented by the following general formula I:

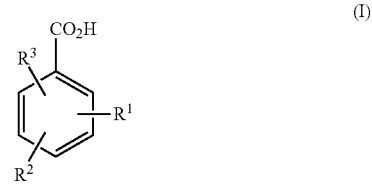

(I)

where $R^1$, $R^2$ and $R^3$ are independently selected from the group consisting of hydrogen, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, phosphonate.

Benzoates are common in nature in the form of natural products and metabolites. Numerous benzoic acid analogs are also used in the food and drug industry. Some of the more abundant benzoates are derivatives with hydroxyl or amino groups or a combination of both. The hydroxyl and amino functions may be present in their free form or capped with another chemical moiety. In certain embodiments of the present technology the other chemical moiety is preferably, but not limited to, methyl or acetyl groups. In some embodiments of the present technology, the phenyl ring may have additional substituents.

Some examples of hydroxybenzoates of the present technology, include but are not limited to, benzoic acid, salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m, p-thymotic acid, diflusinal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, and 3,4,5-trimethoxybenzoic acid.

Some examples of aminobenzoates of the present technology include, but are not limited to, anthranilic acid, 3-aminobenzoic acid, 4,5-dimethylanthranilic acid, N-methylanthranilic acid, N-acetylanthranilic acid, fenamic acids (e.g., tolfenamic acid, mefenamic acid, flufenamic acid), 2,4-diaminobenzoic acid (2,4-DABA), 2-acetylamino-4-aminobenzoic acid, 4-acetylamino-2-aminobenzoic acid, and 2,4-diacetylaminobenzoic acid.

Some examples of aminohydroxybenzoates of the present technology include, but are not limited to, 4-aminosalicylic acid, 3-hydroxyanthranilic acid, and 3-methoxyanthranilic acid.

Heteroaryl Carboxylic Acids

The general structures of some heteroaryl carboxylic acids of the present technology are represented by the following general formula V, VI, VII, VIII, IX, X, XI, XII, or XIII:

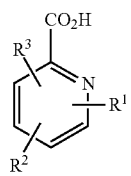
(V)

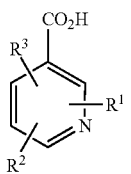
(VI)

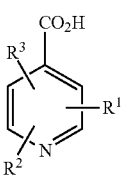
(VII)

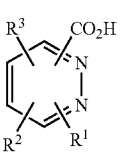
(VIII)

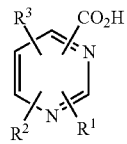
(IX)

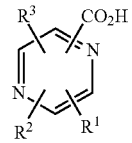
(X)

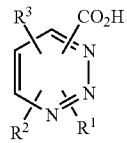
(XI)

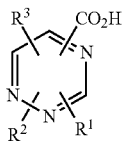
(XII)

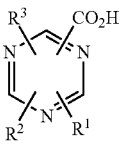
(XIII)

where $R^1$, $R^2$ and $R^3$ are defined as above.

Suitable examples of heteroaryl carboxylic acids of the present technology are pyridine derivatives, some of which are involved in nicotinate and tryptophan metabolism. In these compounds at least one carbon of the phenyl ring is replaced by a nitrogen atom. Besides the carboxyl group, this set of compounds of the present technology can have additional substituents, preferably but not limited to hydroxyl groups.

Some examples of heteroaryl carboxylic acids of the present technology include, but are not limited to, nicotinic acid (niacin), isonicotinic acid, picolinic acid, 3-hydroxypicolinic acid, 6-hydroxynicotinic acid, citrazinic acid, 2,6-dihydroxynicotinic acid, kynurenic acid, xanthurenic acid, 6-hydroxykynurenic acid, 8-methoxykynurenic acid, 7,8-dihydroxykynurenic acid, and 7,8-dihydro-7,8-dihydroxykynurenic acid.

Phenylacetates

Figure 4:
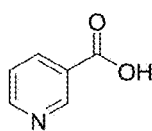
FIG. 4. Example chemical structures of some heteroaryl carboxylic acids for use in the making of the hydromorphone prodrug compositions of the present technology.
Figure 4:
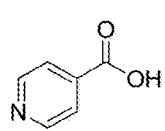
Figure 4:
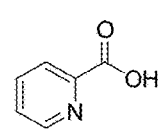
Figure 4:
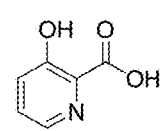
Figure 4:
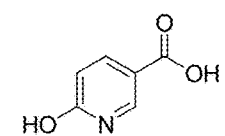
Figure 4:
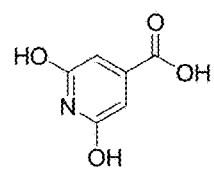
Figure 4:
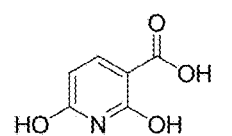
Figure 4:
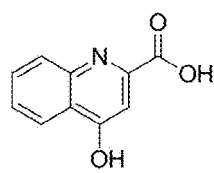
Figure 4:
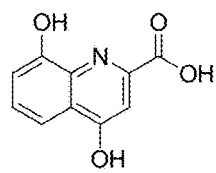
Figure 4:
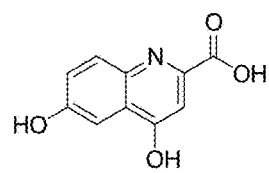
Figure 4:
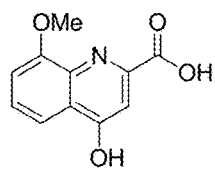
Figure 4:
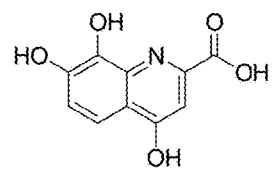
Figure 4:
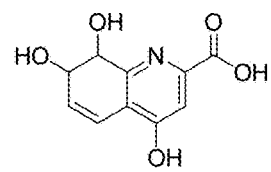

In some embodiments of the present technology, the aryl carboxylic acids of the present technology comprise a carboxylic group that is separated by one carbon from the aryl moiety. These aryl carboxylic acids include branched phenylpropionic acids (i.e., 2-methyl-2-phenylacetates) or other derivatives of phenylacetate (FIG. 4). The general structure of at least one phenylacetate of the present technology is represented by the following general formula II:

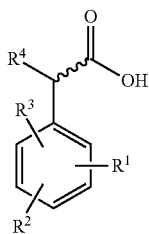

(II)

where $R^1$, $R^2$, $R^3$ and $R^4$ are defined as above.

Phenylacetic acids encompass various subsets of natural products, metabolites and pharmaceuticals. One such pharmaceutically important subset is "profens", a type of NSAIDs and derivatives of certain phenylpropionic acids (e.g., 2-methyl-2-phenylacetic acid analogs). Some other phenylacetates have central functions in the phenylalanine and tyrosine metabolism.

Some examples of phenylacetates of the present technology include, but are not limited to, phenylacetic acid (hydratropic acid), 2-hydroxyphenylacetic acid, 3-hydroxyphenylacetic acid, 4-hydroxyphenylacetic acid, homoprotocatechuic acid, homogentisic acid, 2,6-dihydroxyphenylacetic acid, homovanillic acid, homoisovanillic acid, homoveratric acid, atropic acid, d,l-tropic acid, diclofenac, d,l-mandelic acid, 3,4-dihydroxy-d,l-mandelic acid, vanillyl-d,l-mandelic acid, isovanillyl-d,l-mandelic acid, ibuprofen, fenoprofen, carprofen, flurbiprofen, ketoprofen, and naproxen.

Benzylacetates

Figure 5:
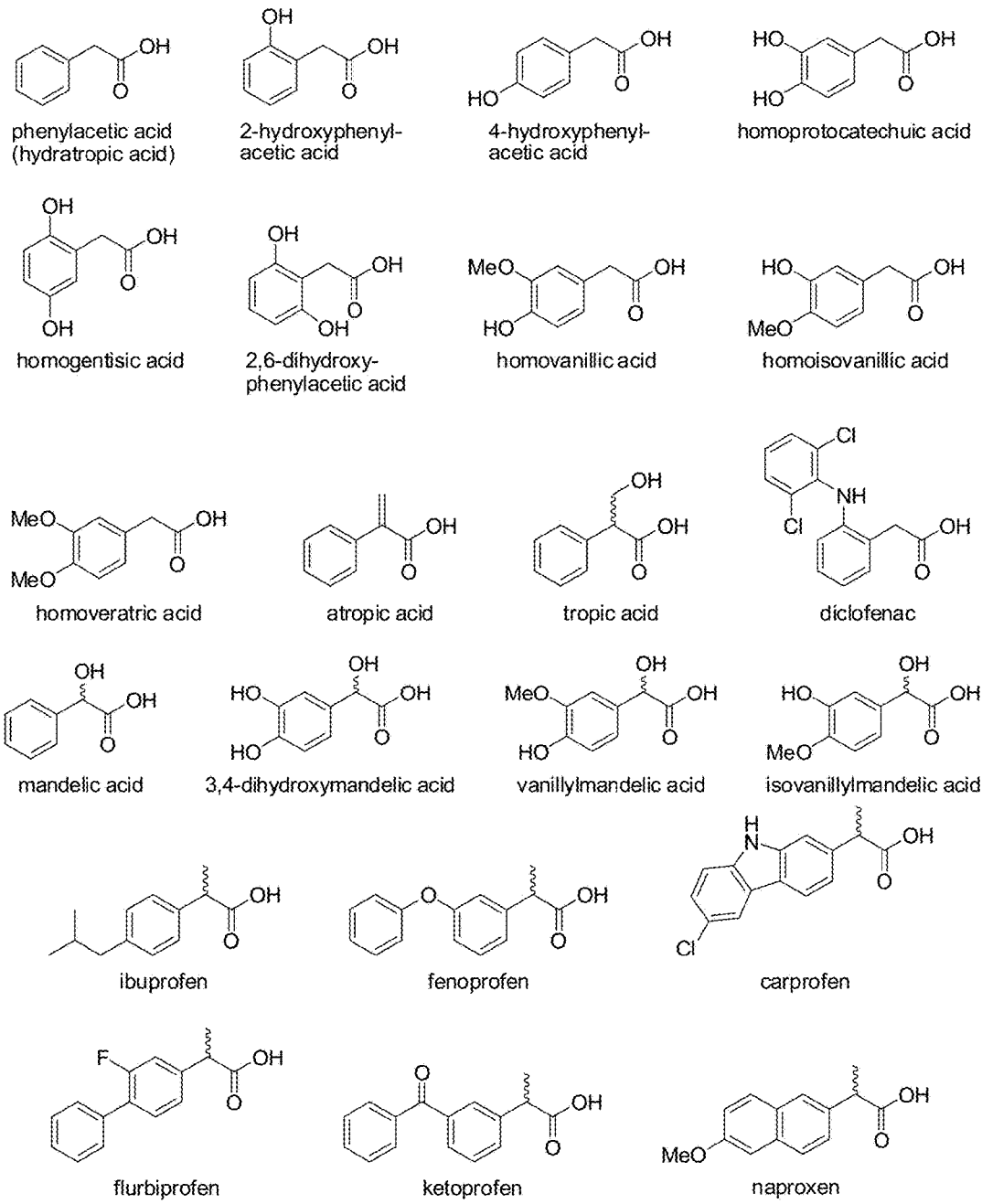
FIG. 5. Example chemical structures of some phenylacetates for use in the making of the hydromorphone prodrug compositions of the present technology.
Figure 6:
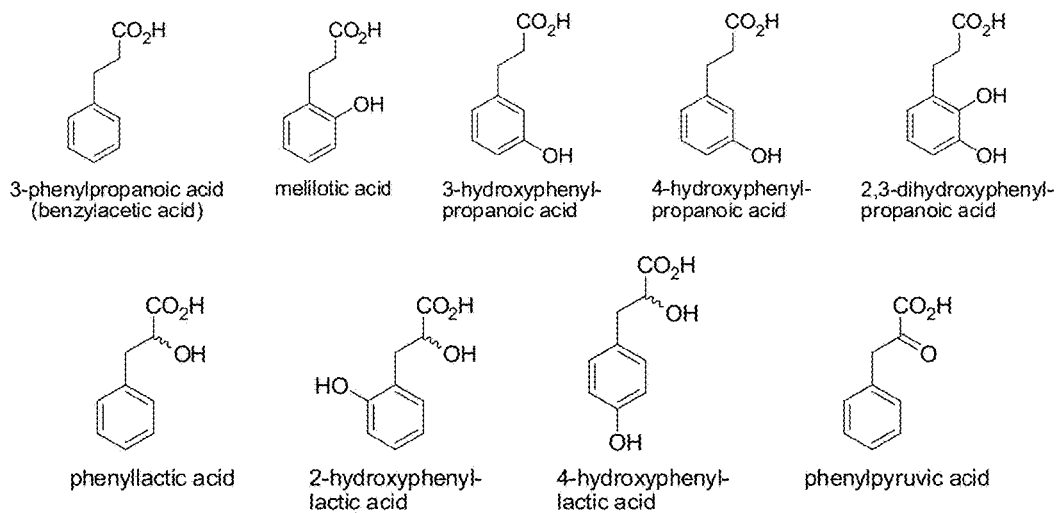
FIG. 6. Example chemical structures of some benzylacetates for use in the making of the hydromorphone prodrug compositions of the present technology.
Figure 7:
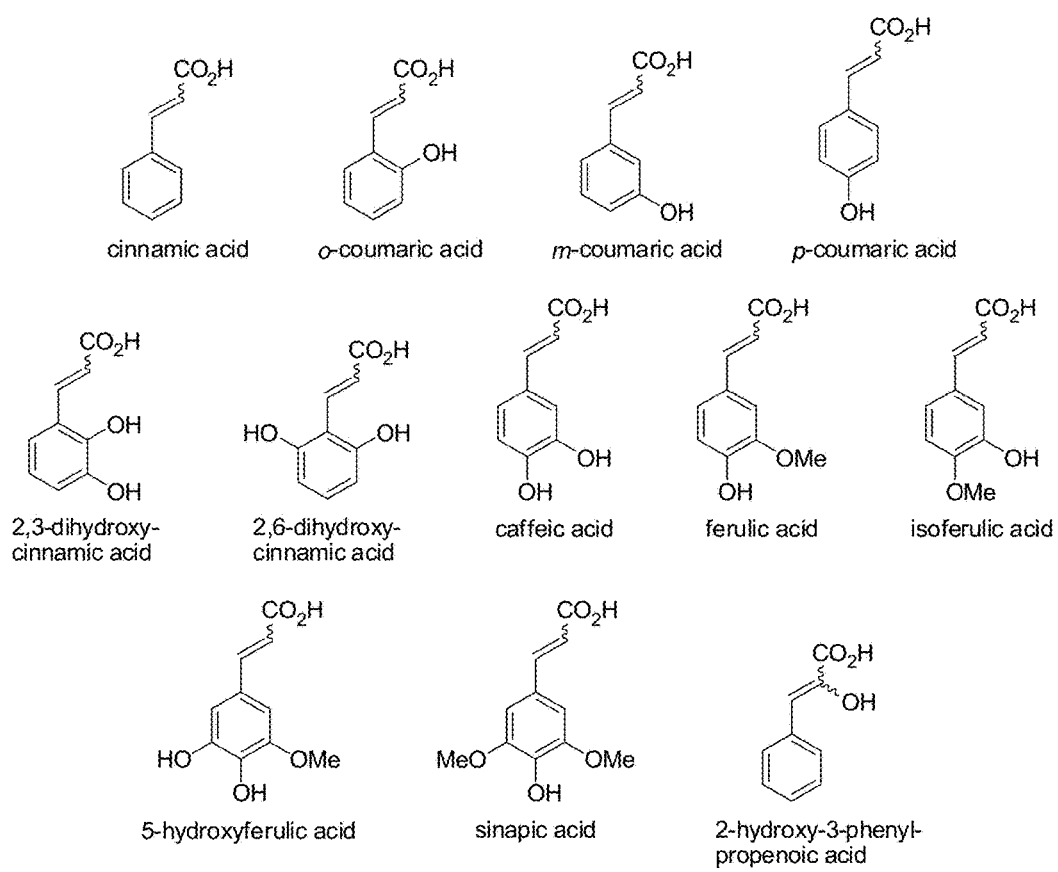
FIG. 7. Example chemical structures of some cinnamates for use in the making of the hydromorphone prodrug compositions of the present technology.
Figure 8:
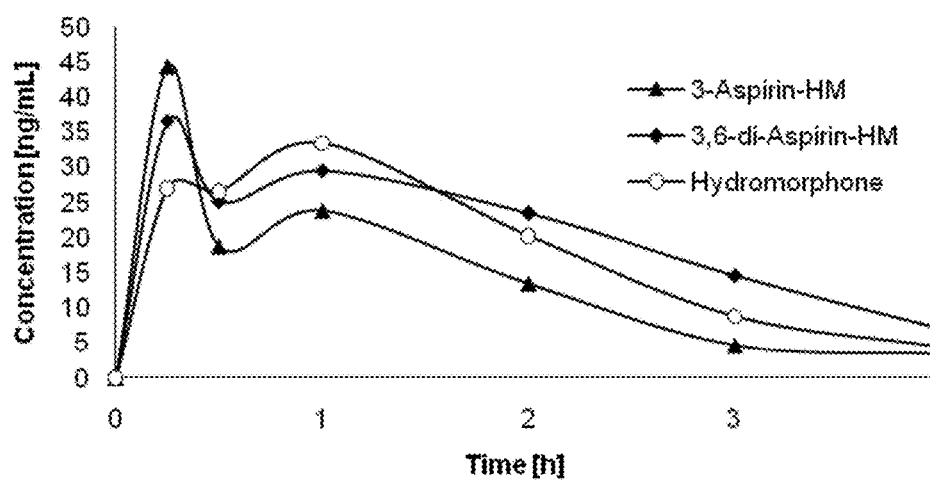
FIG. 8. Pharmacokinetic profile of released hydromorphone (HM) in the plasma of rats that were dosed orally with doses of 3-aspirin-HM, 3,6-di-aspirin-HM and HM equimolar to 2.0 mg/kg of hydromorphone.
Figure 9:
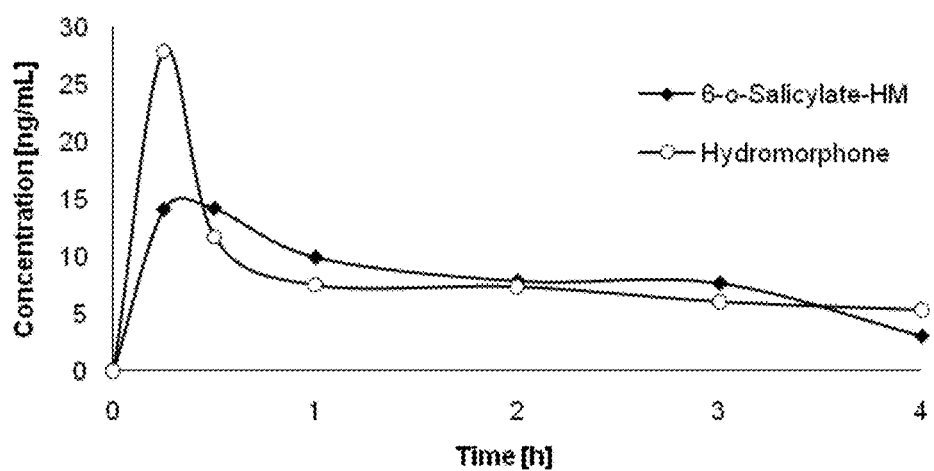
FIG. 9. Pharmacokinetic profile of released hydromorphone (HM) in the plasma of rats that were dosed orally with doses of 6-o-salicylate-HM and HM equimolar to 2.0 mg/kg of hydromorphone.
Figure 10:
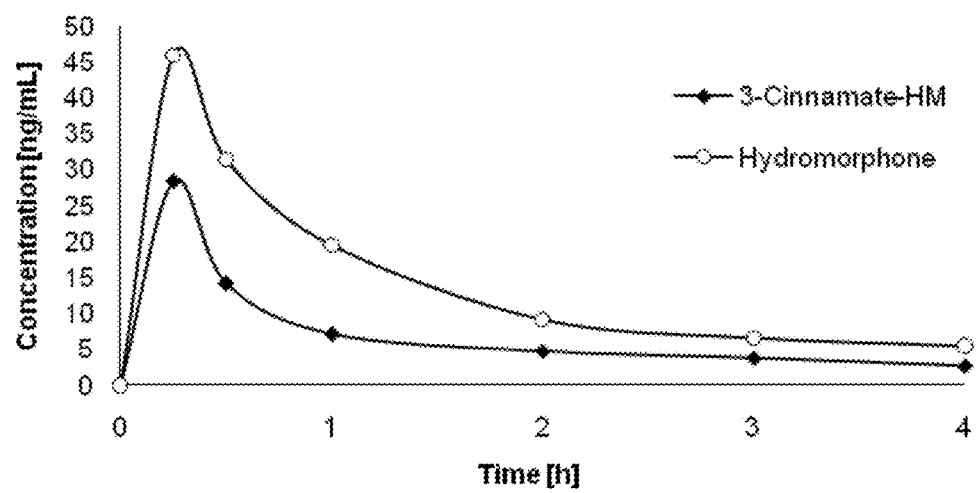
FIG. 10. Pharmacokinetic profile of released hydromorphone (HM) in the plasma of rats that were dosed orally with doses of 3-cinnamate-HM and HM equimolar to 2.0 mg/kg of hydromorphone.
Figure 11:
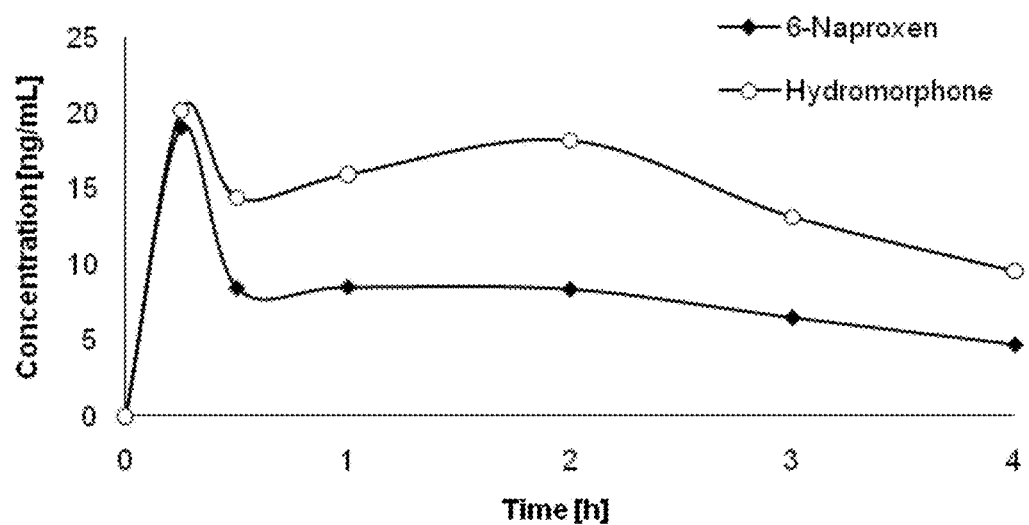
FIG. 11. Pharmacokinetic profile of released hydromorphone (HM) in the plasma of rats that were dosed orally with doses of 6-naproxen-HM and HM equimolar to 2.0 mg/kg of hydromorphone.
Figure 12:
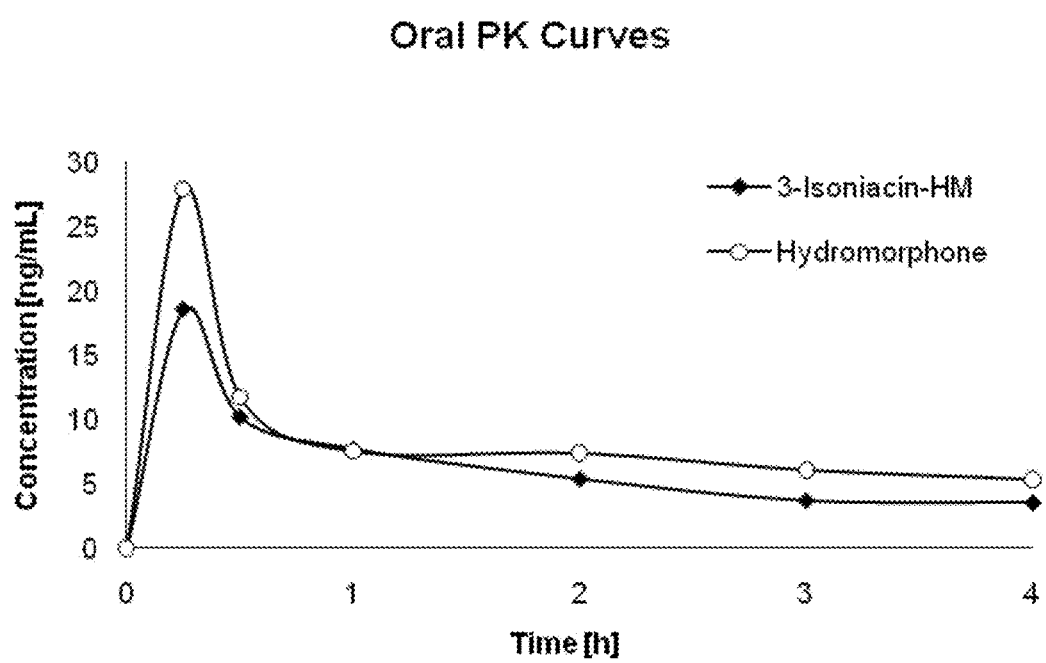
FIG. 12. Pharmacokinetic profile of released hydromorphone (HM) in the plasma of rats that were dosed orally with doses of 3-isoniacin-HM and HM equimolar to 2.0 mg/kg of hydromorphone.
Figure 13:
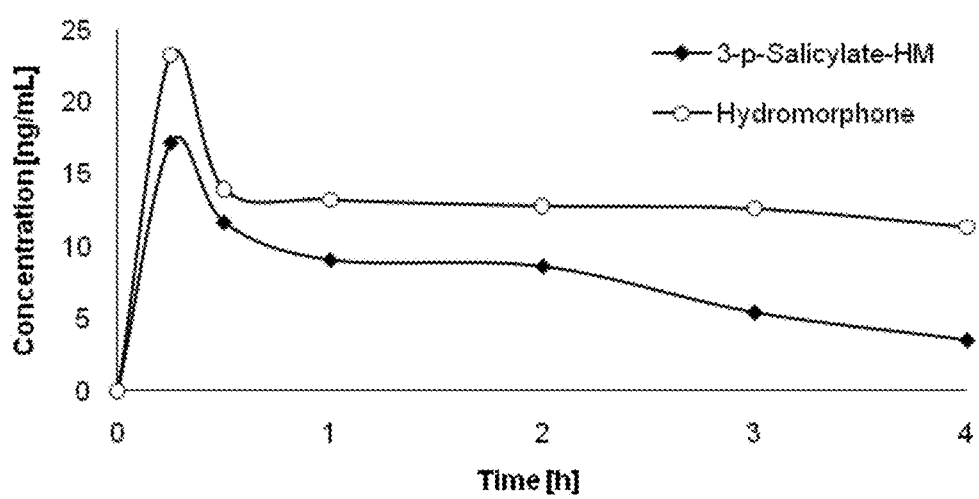
FIG. 13. Pharmacokinetic profile of released hydromorphone (HM) in the plasma of rats that were dosed orally with doses of 3-p-salicylate-HM and HM equimolar to 2.0 mg/kg of hydromorphone.
Figure 14:
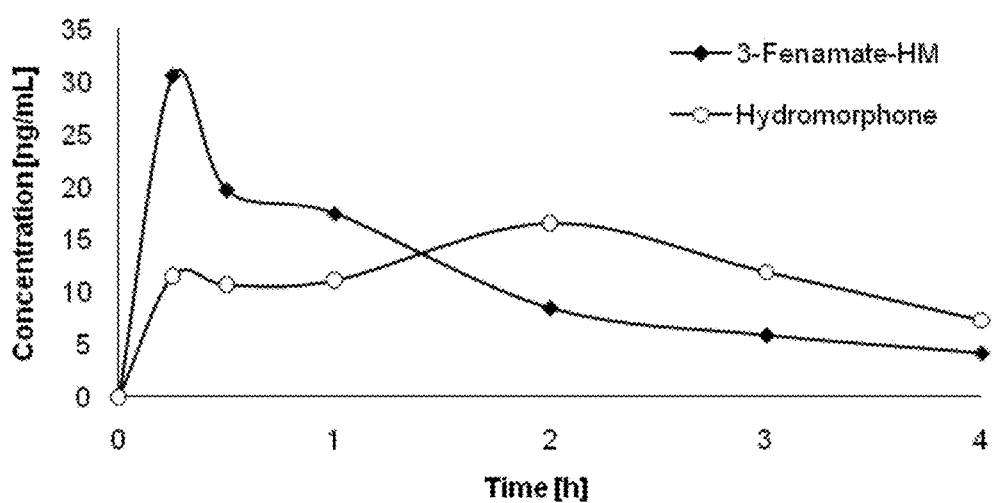
FIG. 14. Pharmacokinetic profile of released hydromorphone (HM) in the plasma of rats that were dosed orally with doses of 3-fenamate-HM and HM equimolar to 2.0 mg/kg of hydromorphone.
Figure 15:
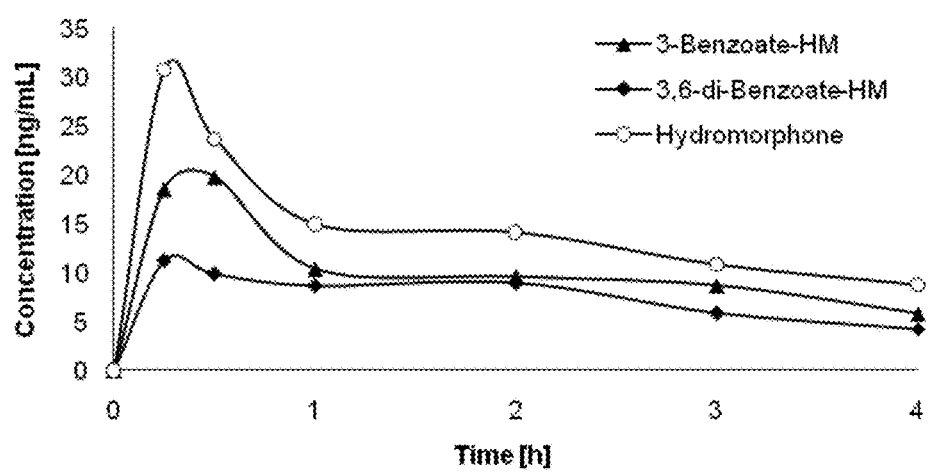
FIG. 15. Pharmacokinetic profile of released hydromorphone (HM) in the plasma of rats that were dosed orally with doses of 3-benzoate-HM, 3,6-di-benzoate-HM and HM equimolar to 2.0 mg/kg of hydromorphone.

In additional embodiments, the aryl carboxylic acids of the present technology comprise a carboxylic group that is separated by two carbons from the aryl moiety. These aryl carboxylic acids include benzylacetates and substituted derivatives thereof and analogs of cinnamic acid (FIG. 5). Both classes of compounds are abundant in nature in the form of natural products or metabolites (e.g., phenylalanine metabolism). The general structures of some benzylacetates and cinnamates of the present technology are represented by the following general formulas (III) and (IV):

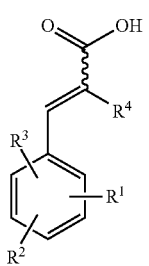

(III)

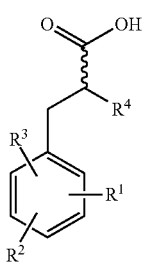

(IV)

where $R^1$, $R^2$, $R^3$ and $R^4$ are defined as above.

Benzylacetic acids are defined by an ethylene group between the carboxyl function and the phenyl ring. Both the alkyl chain and the aryl moiety can have substituents, preferably hydroxyl groups. Some compounds of this class can be found in the phenylalanine metabolism.

Some examples of benzylacetates of the present technology include, but are not limited to, benzylacetic acid, melilotic acid, 3-hydroxyphenylpropanoic acid, 4-hydroxyphenylpropanoic acid, 2,3-dihydroxyphenylpropanoic acid, d,l-phenyllactic acid, o,m,p-hydroxy-d,l-phenyllactic acid, phenylpyruvic acid.

Cinnamates

Cinnamic acids (3-phenylacrylic acids) are unsaturated analogs of benzylacetic acids. Cinnamates occur in two isomeric forms: cis (Z) and trans (E). The cinnamate isomers of certain embodiments of the present technology are preferably, but not limited to, the trans configuration. Similar to benzylacetates, derivatives of cinnamic acid can be substituted on the alkenyl or aryl moiety of the molecule. Preferred substituents of some embodiments of the present technology are hydroxyl and methoxy groups. Certain cinnamates are thought to play a key role in phenylalanine metabolism.

Some examples of cinnamates of the present technology include, but are not limited to, cinnamic acid, o,m,p-coumaric acid, 2,3-dihydroxycinnamic acid, 2,6-dihydroxycinnamic acid, caffeic acid, ferulic acid, isoferulic acid, 5-hydroxyferulic acid, sinapic acid, 2-hydroxy-3-phenylpropenoic acid.

Physiological Benefits

In certain embodiments, the hydromorphone prodrugs and compositions of the present technology can be given orally and, upon administration, release the active hydromorphone after being hydrolyzed in the body. Since the aryl carboxylic acids of this invention are naturally occurring metabolites or mimetics thereof or pharmaceutically active compounds, these prodrugs can be easily recognized by physiological systems resulting in hydrolysis and release of hydromorphone. The prodrugs of the present technology, in certain embodiments, are either not active or have limited pharmacological activity and consequently may follow a metabolic pathway that differs from the parent drug. By choosing suitable aryl carboxylic acids ("ligands") of the present technology the release of hydromorphone into the systemic circulation can be controlled even when the prodrug is administered via routes other than oral.

In at least one embodiment, the hydromorphone prodrugs of the present technology release hydromorphone in a manner that is similar to free or unmodified hydromorphone. In another embodiment, hydromorphone prodrugs of the present technology release hydromorphone in a controlled or sustained form. This controlled release can potentially alleviate certain side effects and improve upon the safety profile of the parent drug. Side effects that are alleviated by the present technology may include, dizziness, lightheadedness, drowsiness, nausea, vomiting, constipation, stomach pain, rash, difficulty urinating, difficulty breathing and fainting.

In addition, hydromorphone and other opioids are also highly addictive and prone to substance abuse. Recreational drug abuse of opioids is a common problem and usually begins with oral doses taken with the purpose of achieving euphoria ("rush", "high"). Over time the drug abuser often increases the oral dosages to attain more powerful "highs" or to compensate for heightened opioid tolerance. Rapid metabolism and fast duration of action of hydromorphone, contributes to its likelihood of being abused. This behavior can escalate and result in exploring of other routes of administration such as intranasal ("snorting") and intravenous ("shooting").

In some embodiments of the present technology, hydromorphone that is conjugated with a suitable aryl carboxylic acid ligand exhibits no rapid spikes in blood levels after oral administration that is sought by a potential drug abuser. In certain embodiments, the prodrugs of the present technology exhibit a delayed $T_{max}$ and lower $C_{max}$ value compared to an equimolar dose of the parent drug. Therefore, the feeling of a "rush" is lacking when prodrugs of the present technology are taken orally even at higher doses while pain relief is still achieved.

In other embodiments, hydromorphone conjugates of the present technology are not hydrolyzed efficiently when administered via non-oral routes. As a result, the prodrugs of the present technology do not generate high plasma or blood concentrations of released hydromorphone when injected or snorted compared to free hydromorphone administered through these routes. Furthermore, since the ligands of certain embodiments of the present technology are bound covalently to hydromorphone, the opioid is not liberated by any type of physical manipulation. This provides an advantage to the prodrugs of the present technology compared to other formulated hydromorphone that release free hydromorphone upon physical manipulation (e.g., grinding, crushing, etc.).

In at least one embodiment, the prodrugs of the present technology have no or insignificant activity at the μ-opioid receptors. In another embodiment, prodrugs of the present technology are not subjected to enzymatic hydrolysis until they are absorbed in the gut. Without being bound by theory, it is believed that the active hydromorphone of the prodrugs of the present technology is effectively "cloaked" by the attached aryl carboxylic acid and may bypass the peripheral μ-opioid receptors without affecting the ENS thereby reducing or preventing OIC.

Hydromorphone is extensively metabolized in the liver to hydromorphone-3-glucuronide (H3G). Although H3G has no analgesic activity, it may cause neuroexcitation, agitation, confusion and hallucinations. If H3G can cross the blood-brain-barrier (BBB), it may accumulate in the central nervous system (CNS) and result in myoclonus, allodynia and seizures as observed in patients dosed chronically with high doses of hydromorphone. This effect may be enhanced in patients with renal dysfunction.

In at least one other embodiment, the prodrugs of the present technology result in decreased conversion of hydromorphone to H3G after oral administration when compared to unconjugated hydromorphone. Without being bound by theory, it is believed that this may result in an improved side effect profile, particularly alleviated neuroexcitatory behaviors compared to free hydromorphone.

Formulations

The compositions and prodrugs of the present technology can be oral dosage forms. These dosage forms include but are not limited to tablet, capsule, softgel, caplet, troche, lozenge, powder, suspension, syrup, solution or oral thin film (OTF). Preferred oral administration forms are capsule, tablet, solutions and OTF.

The compositions and prodrugs of the present technology can also be solid dosage forms that include excipients. Excipients of the present technology include, but are not limited to, antiadherents, binders, coatings, disintegrants, fillers, flavors and colors, glidants, lubricants, preservatives, sorbents and sweeteners.

Oral formulations of the present technology can also be included in a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a patient that is unable to swallow.

Softgel or soft gelatin capsules may be prepared, for example by dispersing the formulation in an appropriate vehicle (vegetable oils are commonly used) to form a high viscosity mixture. This mixture is then encapsulated with a gelatin based film using technology and machinery known to those in the soft gel industry. The individual units so formed are then dried to constant weight.

Chewable tablets, for example, may be prepared by mixing the formulations with excipients designed to form a relatively soft, flavored, tablet dosage form that is intended to be chewed rather than swallowed. Conventional tablet machinery and procedures, for example, direct compression and granulation, i.e., slugging, before compression, can be utilized. Those individuals involved in pharmaceutical solid dosage form production are versed in the processes and the machinery used, as the chewable dosage form is a very common dosage form in the pharmaceutical industry.

Film coated tablets, for example, may be prepared by coating tablets using techniques such as rotating pan coating methods or air suspension methods to deposit a contiguous film layer on a tablet.

Compressed tablets, for example may be prepared by mixing the formulation with excipients intended to add binding qualities to disintegration qualities. The mixture is either directly compressed or granulated and then compressed using methods and machinery known to those of skill in the industry. The resultant compressed tablet dosage units are then packaged according to market need, for example, in unit dose, rolls, bulk bottles, blister packs, etc.

The present technology also contemplates the use of biologically-acceptable carriers which may be prepared from a wide range of materials. Without being limited to, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders of the present technology may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons working in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

It should be understood that in addition to the ingredients particularly mentioned above, the formulations of the present technology can include other suitable agents such as flavoring agents, preservatives and antioxidants. Such antioxidants would be food acceptable and could include vitamin E, carotene, BHT or other antioxidants.

Other compounds which may be included by admixture are, for example, medically inert ingredients, e.g., solid and liquid diluents, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulfates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or syrup, in capsules or sachets in the dry state, in a non-aqueous suspension wherein suspending agents may be included, or in a suspension in water or syrup. Where desirable, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. In particular syrup for diabetic patients can contain as carriers only products, for example sorbitol, which do not metabolize to glucose or which metabolize only a very small amount to glucose. The suspensions and the emulsions may contain a carrier, for example a natural gum, agar, sodium alginate, pectin, methylcellulose, carboxymethylcellulose or polyvinyl alcohol.

Current approved formulations of hydromorphone are tablets, capsules, modified release capsules, extended release tablets, controlled release capsules, suppository, powder for injection, oral liquid, cough syrup, and injections. The conjugated hydromorphone of the present technology, in certain embodiments, can be formulated into any of these currently approved unconjugated hydromorphone formulations.

Other current approved formulations of hydromorphone are combination therapies of hydromorphone and one or more other non-narcotic active ingredient depending on intended indication. Examples of these active pharmaceuticals include, but are not limited to, acetaminophen, ibuprofen, and aspirin. The conjugated hydromorphone of the present technology can be formulated with one or a combination of these or other active substances or as a standalone active ingredient without any other actives.

Methods of Use

The conjugate compositions or prodrugs of the present technology may be used in methods of treating a patient having a disease, disorder or condition requiring or mediated by binding or inhibiting binding of an opioid to the opioid receptors of the patient. Treatment comprises orally administering to the patient at least one conjugate of hydromorphone as described in the present technology in an amount therapeutically equivalent to an effective amount of unconjugated hydromorphone. The conjugate can exhibit reduced peak plasma concentrations ($C_{max}$) and lower area under the curve (AUC) of released hydromorphone when administered via non-oral routes, such as intranasal and intravenous, compared to an equivalent molar amount of unconjugated hydromorphone. In some aspects, oral administration of at least one conjugate can provide an extended rate of release of hydromorphone over time and a therapeutically bioequivalent AUC with little or no spike in $C_{max}$ or equivalent $C_{max}$ value when compared to other controlled release forms of hydromorphone (e.g., Exalgo®). In other embodiments, at least one conjugate can exhibit less variability in plasma concentrations of hydromorphone after oral administration when compared to unconjugated hydromorphone.

In other embodiments, at least one conjugate is provided in an amount sufficient to provide a therapeutically bioequivalent AUC (area under the curve) of hydromorphone when compared to a molar equivalent amount of unconjugated hydromorphone. In further embodiments, the conjugate is provided in an amount sufficient to provide a therapeutically bioequivalent AUC of hydromorphone when compared to a molar equivalent amount of unconjugated hydromorphone but has a lower $C_{max}$ (peak concentration) value of hydromorphone in plasma or does not provide an equivalent $C_{max}$ value in plasma. In some aspects, the conjugate is provided in an amount sufficient to provide a therapeutically bioequivalent $C_{max}$ value of hydromorphone when compared to a molar equivalent amount of unconjugated hydromorphone. In further embodiments, at least one conjugate is provided in an amount sufficient to provide an increased AUC or increased $C_{max}$ value of hydromorphone, or both, when compared to a molar equivalent amount of unconjugated hydromorphone.

In further aspects, at least one conjugate is provided in an amount therapeutically equivalent to an effective amount of unconjugated hydromorphone but reduces or prevents opioid induced constipation (OIC). In some embodiments, at least one conjugate is provided in an amount therapeutically equivalent to an effective amount of unconjugated hydromorphone but decreases or prevents neuroexcitatory toxicity caused by hydromorphone-3-glucuronide.

Suitable diseases, disorders or conditions that can be treated by the prodrugs or compositions of the present technology are narcotic or drug addiction, acute or chronic pain and severe coughs.

Dosages for the conjugates of the present technology depend on their molecular weight and the respective weight-percentage of hydromorphone as part of the whole conjugate, and therefore can be higher than the dosages of free hydromorphone.

Adult oral dosage strengths based on hydromorphone hydrochloride range between 2 mg and 16 mg per dose for immediate release and 8 mg to 64 mg per dose for extended release formulations. Pediatric oral doses range from 0.03 mg/kg/dose to 0.08 mg/kg/dose for children and adolescents less than 50 kg and 1 mg to 2 mg per dose for pediatrics greater than 50 kg. Pediatric oral doses for cough suppression range from 0.5 mg to 1 mg per dose. Doses should be titrated to appropriate analgesic effects while minimizing adverse effects. Dosages for the prodrugs of the present technology can be higher depending on their molecular weight and the respective weight-percentage of hydromorphone as part of the whole conjugate. Dose conversion from hydromorphone hydrochloride to hydromorphone prodrug can be performed using the following formula:

$$\text{dose}(HM\ \text{prodrug}) = f_{BA} \times \text{dose}(HM \cdot \text{HCl}) \times \frac{\text{MW}(HM\ \text{prodrug})}{321.80\ \frac{g}{mol}}$$

HM=hydromorphone
HCl=hydrochloride
MW=molecular weight $f_{BA}$=correction factor accounting for differences in bioavailability between unmodified hydromorphone and prodrugs of this invention. This correction factor is specific for each prodrug of the present technology.

Suitable dosages of the conjugated hydromorphone of the present technology include, but are not limited to, formulations including from about 0.1 mg or higher, alternatively from about 0.5 mg or higher, alternatively from about 2.5 mg or higher, alternatively from about 5.0 mg or higher, alternatively from about 7.5 mg or higher, alternatively from about 10 mg or higher, alternatively from about 20 mg or higher, alternatively from about 30 mg or higher, alternatively from about 40 mg or higher, alternatively from about 50 mg or higher, alternatively from about 60 mg or higher, alternatively from about 70 mg or higher, alternatively from about 80 mg or higher, alternatively from about 90 mg or higher, alternatively from about 100 mg or higher, alternatively from about 150 mg or higher, alternatively from about 200 mg or higher, and include any additional increments thereof, for example, 0.1, 0.2, 0.25, 0.3, 0.4, 0.5, 0.6, 0.7, 0.75, 0.8, 0.9 or 1.0 mg and multiplied factors thereof, (e.g., ×1, ×2, ×2.5, ×5, ×10, ×100, etc).

In another aspect, the amount per unit dose is based on the content of free or unconjugated hydromorphone in the conjugate of hydromorphone.

The present technology also includes dosage formulations including currently approved formulations of hydromorphone, where the dosage can be calculated using the above-noted formula determined by the amount of hydromorphone. The present technology provides for dosage forms formulated as a single therapy or as a combination therapy with other active pharmaceutical ingredients (APIs).

The prodrugs of the present technology may be administered for the relief of pain or cough depression or for the treatment of any condition that may require the blocking of opioid receptors.

The conjugates of the present technology can provide a decrease in side effects of the opioid analgesic, including reduced or inhibited constipatory effects.

General Synthetic Procedures

The present technology also provides a method of synthesis for the preparation of the conjugated hydromorphone of the present technology. In certain embodiments, the synthesis of the prodrugs of the present technology includes the steps of:

Phenol ester conjugates (3-ligand-HM):
1. Protection of the ligand, if necessary.
2. Activation of the ligand carboxylic acid group, if necessary.
3. Addition of the activated ligand to hydromorphone or vice versa in the presence of base.
4. Removal of ligand protecting group(s), if applicable.

Enol ester conjugates (6-ligand-HM):
1. Protection of the ligand, if necessary.
2. Activation of the ligand carboxylic acid group, if necessary.
3. Protection of the phenolic (3-OH) hydroxyl group of hydromorphone, if necessary.
4. Addition of the activated ligand to hydromorphone or vice versa in the presence of base.
5. Removal of ligand and/or hydromorphone protecting group(s), if applicable.

Phenol ester/enol ester di-conjugates (3,6-di-ligand-HM):
1. Protection of the ligand, if necessary.
2. Activation of the ligand carboxylic acid group, if necessary.
3. Addition of the activated ligand to hydromorphone or vice versa in the presence of base.
4. Removal of ligand protecting group(s), if applicable.

If the aryl carboxylic acid contains any additional reactive functional groups that may interfere with the coupling to hydromorphone, it may be necessary to first attach one or more protecting groups. Any suitable protecting group may be used depending on the type of functional group and reaction conditions. Some protecting group examples are: acetyl (Ac), β-methoxyethoxymethyl ether (MEM), methoxymethyl ether (MOM), p-methoxybenzyl ether (PMB), trimethylsilyl (TMS), tert.-butyldimethylsilyl (TBDPS), triisopropylsilyl (TIPS), carbobenzyloxy (Cbz), p-methoxybenzyl carbonyl (Moz), tert.-butyloxycarbonyl (Boc), 9-fluorenylmethyloxycarbonyl (Fmoc), benzyl (Bn), p-methoxybenzyl (MPM), tosyl (Ts). Temporary formation of acetals or ketals from carbonyl functions may also be appropriate.

The carboxylic acid group of the ligands may need to be activated in order to react with hydromorphone and to generate appreciable amounts of conjugate. This activation can be accomplished in numerous ways by a variety of coupling agents known to one skilled in the art. Examples of such coupling agents are: N,N'-dicyclohexylcarbodiimide (DCC), N-(3-dimethylaminopropyl)-N'-ethylcarbodiimide (EDCI), N,N'-diisopropylcarbodiimide (DIC), 1,1'-carbonyldiimidazole (CDI) or other carbodiimides; (benzotriazol-1-yloxy)tris(dimethylamino)phosphonium hexafluorophosphate (BOP), bromotripyrrolidinophosphonium hexafluorophosphate (PyBroP), (benzotriazol-1-yloxy)tripyrrolidinophosphonium hexafluorophosphate (PyBOP) or other phosphonium-based reagents; O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), fluoro-N,N,N',N'-tetramethylformamidinium hexafluorophosphate (TFFH), N,N,N',N'-tetramethyl-O—(N-succinimidyl) uronium tetrafluoroborate (TSTU) or other aminium-based reagents. The aryl carboxylic acid can also be converted to a suitable acyl halide, acyl azide or mixed anhydride.

A base may be required at any step in the synthetic scheme of an aryl carboxylic acid conjugate of hydromorphone. Suitable bases include but are not limited to: 4-methylmorpholine (NMM), 4-(dimethylamino)pyridine (DMAP), N,N-diisopropylethylamine, lithium bis(trimethylsilyl)amide, lithium diisopropylamide (LDA), any alkali metal tert.-butoxide (e.g., potassium tert.-butoxide), any alkali metal hydride (e.g., sodium hydride), any alkali metal alkoxide (e.g., sodium methoxide), triethylamine or any other tertiary amine.

Suitable solvents that can be used for any reaction in the synthetic scheme of an aryl carboxylic acid conjugate of hydromorphone include but are not limited to: acetone, acetonitrile, butanol, chloroform, dichloromethane, dimethylformamide (DMF), dimethylsulfoxide (DMSO), dioxane, ethanol, ethyl acetate, diethyl ether, heptane, hexane, methanol, methyl tert.-butyl ether (MTBE), isopropanol, isopropyl acetate, diisopropyl ether, tetrahydrofuran, toluene, xylene or water.

Pharmaceutical Kits

The present technology also provides pharmaceutical kits for the treatment or prevention of drug withdrawal symptoms or pain in a patient. The patient may be a human or animal patient. Suitable human patients include pediatric patients, geriatric (elderly) patients, and normative patients. The kit comprises a specific amount of the individual doses in a package containing a pharmaceutically effective amount of at least one conjugate of hydromorphone of the present technology. The kit can further include instructions for use of the kit. The specified amount of individual doses may contain from about 1 to about 100 individual dosages, alternatively from about 1 to about 60 individual dosages, alternatively from about 10 to about 30 individual dosages, including, about 1, about 2, about 5, about 10, about 15, about 20, about 25, about 30, about 35, about 40, about 45, about 50, about 55, about 60, about 70, about 80, about 100, and include any additional increments thereof, for example, 1, 2, 5, 10 and multiplied factors thereof, (e.g., ×1, ×2, ×2.5, ×5, ×10, ×100, etc).

The presently described technology and its advantages will be better understood by reference to the following examples. These examples are provided to describe specific embodiments of the present technology. By providing these specific examples, it is not intended limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Example 1: Oral Pharmacokinetic Study

Certain prodrug conjugates of the present technology were dosed as oral solutions in rats and compared to an equimolar solution of hydromorphone hydrochloride. The oral studies were performed at doses equimolar to 2.0 mg/kg of hydromorphone. The release of hydromorphone from the prodrugs varied depending on the ligand attached to hydromorphone. Exposures to hydromorphone released from the prodrugs in the presented examples ranged from 45%-AUC to 113% %-AUC, %-$C_{max}$ from 37% to 185% and %-$T_{max}$ from 13% to 200% compared to unconjugated hydromorphone hydrochloride. The PK profile curves are presented in FIGS. 8-15 and the PK parameters are summarized in Table 1 below.

TABLE 1

PK parameters of hydromorphone released from the hydromorphone conjugates (rat studies).

| Conjugate | AUC [ng/mL × h] | $C_{max}$ [ng/mL] | $T_{max}$ [h] | %-AUC of HM | %-$C_{max}$ of HM | %-$T_{max}$ of HM |
|---|---|---|---|---|---|---|
| 3-Aspirin-HM | 55.9 | 44.3 | 0.250 | 76% | 133% | 25% |
| 3,6-di-Aspirin-HM | 82.4 | 36.5 | 0.250 | 113% | 109% | 25% |
| 6-o-Salicylate-HM | 33.3 | 14.1 | 0.250 | 101% | 51% | 100% |
| 3-Cinnamate-HM | 25.3 | 28.3 | 0.250 | 45% | 62% | 100% |
| 6-Naproxen-HM | 31.6 | 19.1 | 0.250 | 54% | 94% | 100% |
| 3-Isoniacin-HM | 25.1 | 18.5 | 0.250 | 76% | 66% | 100% |
| 3-p-Salicylic-HM | 31.4 | 17.2 | 0.250 | 60% | 74% | 100% |
| 3-Fenamate-HM | 44.6 | 30.6 | 0.250 | 94% | 185% | 13% |
| 3-Benzoate-HM | 41.2 | 19.8 | 0.500 | 72% | 64% | 200% |
| 3,6-di-Benzoate-HM | 30.1 | 11.3 | 0.250 | 53% | 37% | 100% |

The hydromorphone plasma concentrations produced by 3-cinnamate-HM, 3-p-salicylate-HM, 3-benzoate-HM and 3,6-di-benzoate-HM were lower at all time points when compared to unconjugated hydromorphone. The $C_{max}$ value of hydromorphone released from 6-naproxen-HM was similar to the peak plasma concentration of unconjugated hydromorphone, but the overall exposure after oral administration of this conjugate was reduced significantly compared to the parent drug. The hydromorphone plasma concentrations generated by 6-o-salicylate-HM and 3-isoniacin-HM were similar to unconjugated hydromorphone, except for a considerable decrease at the first time point (0.25 hours) resulting in a lower $C_{max}$ value for these two conjugates. The plasma concentrations of hydromorphone released from 3-fenamate-HM were elevated for the first hour after oral administration and then decreased quickly when compared to unconjugated hydromorphone. The hydromorphone plasma concentrations were comparable after oral administration of 3-aspirin-HM, 3,6-di-aspirin-HM and unconjugated hydromorphone.

Example 2: Intranasal Pharmacokinetic Study

Certain prodrug conjugates of the present technology were dosed as intranasal solutions in rats and compared to an equimolar solution of hydromorphone hydrochloride. The intranasal studies were performed at doses equimolar to 2.0 mg/kg of hydromorphone. The release of hydromorphone from the prodrugs varied depending on the ligand attached to hydromorphone.

Figure 16:
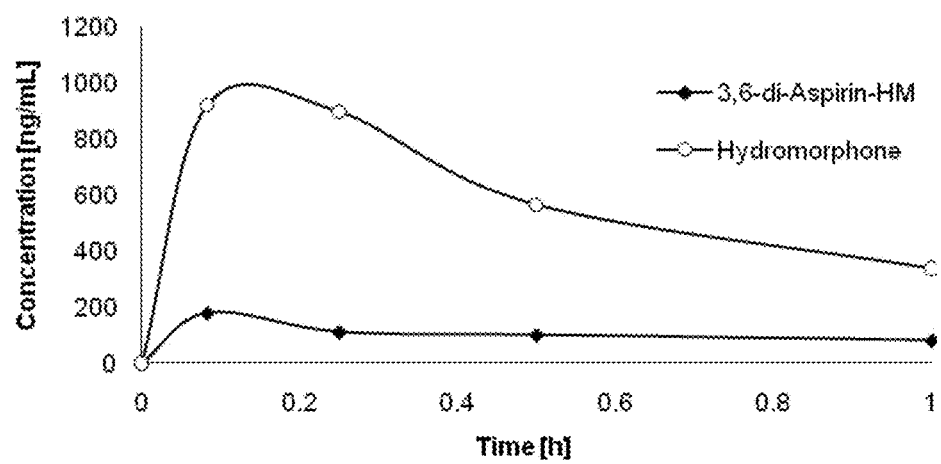
FIG. 16. Pharmacokinetic profile of released hydromorphone (HM) in the plasma of rats that was dosed intranasally with doses of 3,6-di-aspirin-HM and HM equimolar to 2.0 mg/kg of hydromorphone.

Plasma concentrations of hydromorphone after intranasal administration of 3,6-di-aspirin-HM were significantly reduced when compared to the parent drug (FIG. 16). The AUC and $C_{max}$ values of 3,6-di-aspirin-HM were 17% and 20% of the respective PK parameters of unconjugated hydromorphone.

Example 3: Intravenous Pharmacokinetic Study

Certain prodrug conjugates of the present technology were dosed as intravenous solutions in rats and compared to an equimolar solution of hydromorphone hydrochloride. The release of hydromorphone from the prodrugs varied depending on the ligand attached to hydromorphone.

Figure 17:
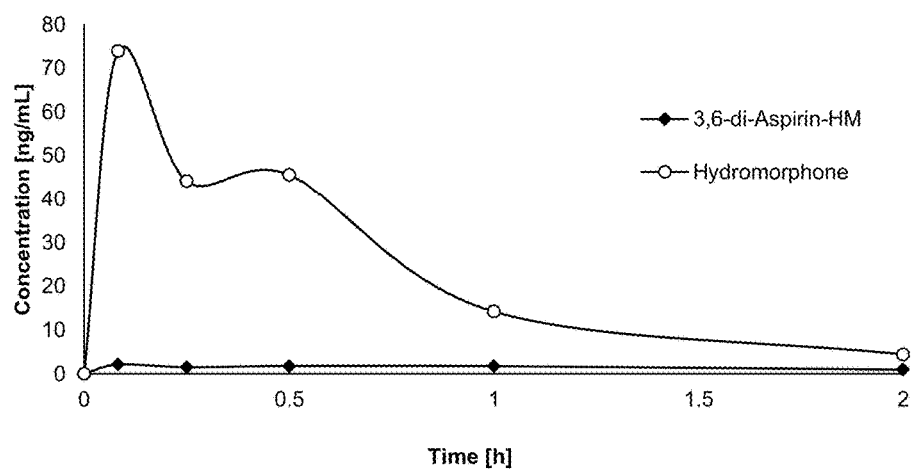
FIG. 17. Pharmacokinetic profile of released hydromorphone (HM) in the plasma of rats that was dosed intravenously with doses of 3,6-di-aspirin-HM and HM equimolar to 0.2 mg/kg of hydromorphone.

Hydromorphone and 3,6-di-aspirin-HM were dosed intravenously in rats at 0.20 mg/kg. Plasma concentrations of hydromorphone after intravenous administration of 3,6-di-aspirin-HM were significantly lower when compared to unconjugated hydromorphone (FIG. 17). The AUC and $C_{max}$ values of 3,6-di-aspirin-HM were 6% and 3% of the respective PK parameters of unconjugated hydromorphone.

Example 4: Dose Escalation Study

Figure 18:
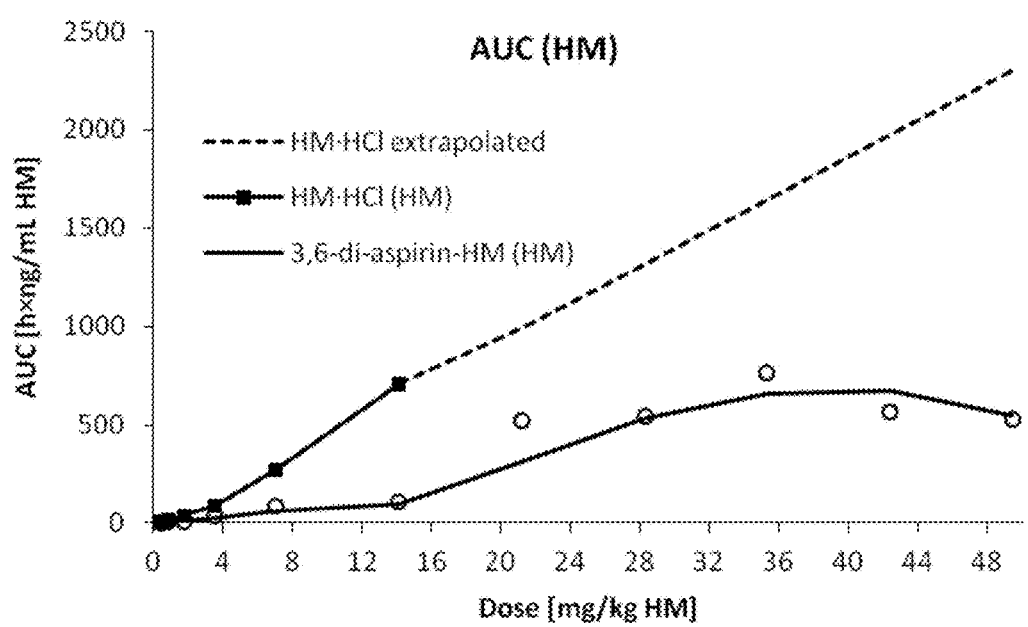
FIG. 18. Area under the curve (AUC) of released hydromorphone (HM) in the plasma of rats that were dosed orally with escalating equimolar doses of HM and 3,6-di-aspirin-HM.

Certain prodrug conjugates of the present technology were dosed at escalating dosages as oral solutions in rats. When 3,6-di-aspirin-HM was dosed above the therapeutic level, the exposure (AUC) to hydromorphone reached a plateau. However, after oral administration of hydromorphone hydrochloride, the exposure (AUC) to hydromorphone remained approximately dose proportional even above the therapeutic level and caused death of the test animals with dosages above 14 mg/kg (see FIG. 18). These data suggest that 3,6-di-aspirin-HM has a decreased potential for causing overdose when compared to hydromorphone hydrochloride.

Without being bound by theory, it is believed that the exposure (AUC) plateau seen when 3,6-di-aspirin-HM was dosed above the therapeutic level is due to saturation of hydrolytic enzymes.

Example 5: Tamper Resistance Study

Certain prodrug conjugates of the present technology were exposed to various commonly applied "extraction methods" to test for hydrolysis and/or decomposition of the prodrug. Solvent extraction of 3,6-di-aspirin-HM from formulation only yielded inactive prodrug with inherent pharmacological abuse protection. This shows that hydromorphone cannot be released from 3,6-di-aspirin-HM through physical manipulation or solvent extraction. In addition, 3,6-di-aspirin-HM is chemically stable under commonly applied "extraction methods" and only hydrolyzed and/or decomposed under extremely harsh conditions yielding a complex mixture of decomposition products in highly acidic or caustic solutions. Additionally, the decomposition products exhibited reduced oral, IN and IV bioavailability making extraction inefficient and impractical. The results of the extraction study are summarized in Table 2 below.

TABLE 2

Release of 3,6-di-aspirin-HM from formulation

| Condition | Ambient Temperature | |
|---|---|---|
| (Common Methods) | 30 min. | 60 min. |
| 1N HCl | 0 | 0 |
| Glacial acetic acid | 0 | 0 |
| 5% Acetic acid | 0 | 0 |
| Water | 0 | 0 |
| Sat. NaHCO$_3$ | 0 | 0 |
| 1N NaOH | 1% | 1% |
| 4N NaOH | 1% | 6% |

Numbers represent amount of hydromorphone released from 3,6-di-aspirin-HM (as %-AUC by HPLC)

Figure 19:
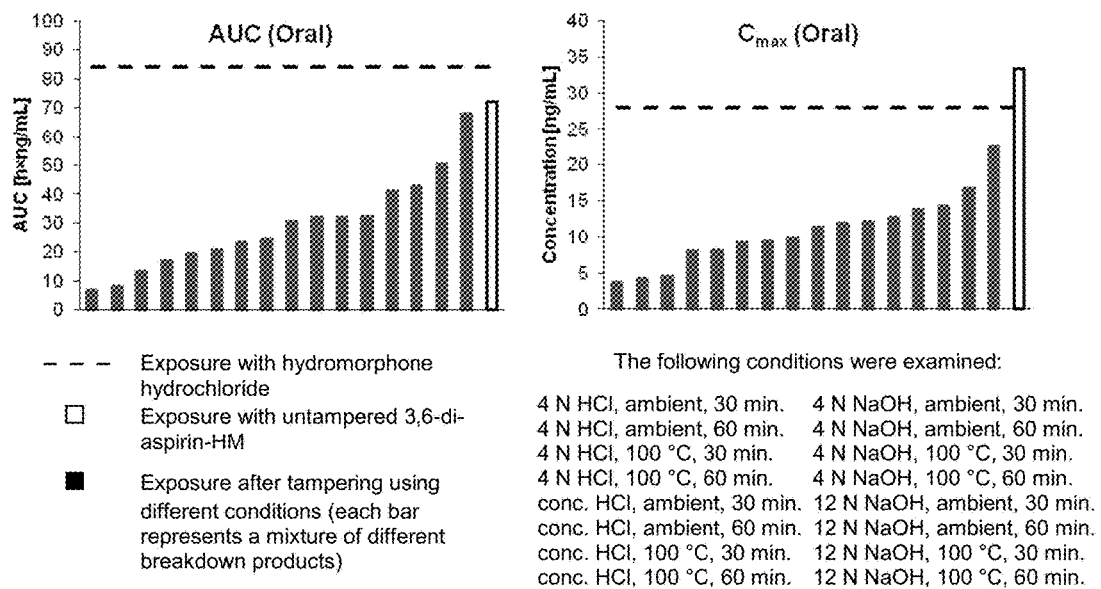
FIG. 19. Area under the curve (AUC) and peak plasma concentrations ($C_{max}$) in the plasma of rats that were dosed orally with equimolar doses of HM, untampered 3,6-di-aspirin-HM, and hydrolytic breakdown products of 3,6-di-aspirin-HM.

In addition, 3,6-di-aspirin-HM was exposed to 16 harsh, hydrolytic conditions and the resulting breakdown products were monitored and quantified by HPLC. Besides hydromorphone, three intermediate breakdown products were observed and then synthesized and dosed orally in rats. For each hydrolytic condition, virtual AUC and $C_{max}$ values were calculated based on the composition of the observed mixture and on the individual PK parameters for each of its components (see FIG. 19). These data show that tampering with 3,6-di-aspirin-HM produces a mixture of compounds that when taken orally results in exposure (AUC) of hydromorphone that is lower than the exposure (AUC) seen with hydromorphone hydrochloride or untampered 3,6-di-aspirin-HM and in a maximum exposure ($C_{max}$) of hydromorphone that is lower than the maximum exposure ($C_{max}$) seen with hydromorphone hydrochloride.

Example 6: Opioid Induced Constipation Study

Receptor binding assays and validated rat gastrointestinal (GI) motility studies were performed with certain prodrug conjugates of the present technology. The receptor binding assays showed that 3,6-di-aspirin-HM has insignificant affinity to the enteric μ-opioid receptors that are located in the gut.

Figure 20:
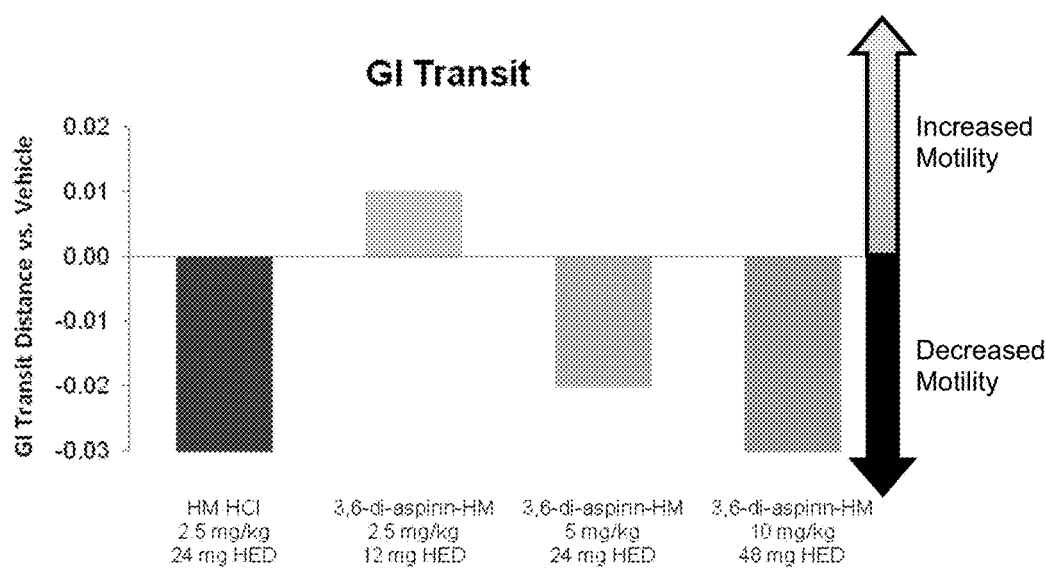
FIG. 20. Gastrointestinal (GI) transit distance from validated rat motility study of rats dosed orally with equimolar doses of HM and 3,6-di-aspirin-HM.

The validated rat motility study demonstrated that at equimolar does, 3,6-di-aspirin-HM reduces GI transit to a lesser extent than hydromorphone hydrochloride. The effect of 3,6-di-aspirin-HM on motility was similar to hydromorphone hydrochloride only when 3,6-di-aspirin-HM was given at twice the equimolar dose of the parent drug (FIG. 20). This data suggests that 3,6-di-aspirin-HM possesses the potential to reduce or eliminate the opioid-induced constipation (OIC) associated with administration of unconjugated hydromorphone.

Without being bound by theory, it is believed that 3,6-di-aspirin-HM stays mostly intact until absorbed into the intestinal mucosa where it is converted to hydromorphone after bypassing the peripheral opioid receptors. Again, without being bound by theory, it is also believed that the released hydromorphone subsequently passes through the basolateral membrane into the systemic circulation. This theoretical mechanism is consistent with the potential for reduction or prevention of opioid-induced constipation associated with administration of 3,6-di-aspirin-HM compared to unconjugated hydromorphone.

Example 7: Certain Synthetic Schemes

Figure 21A:
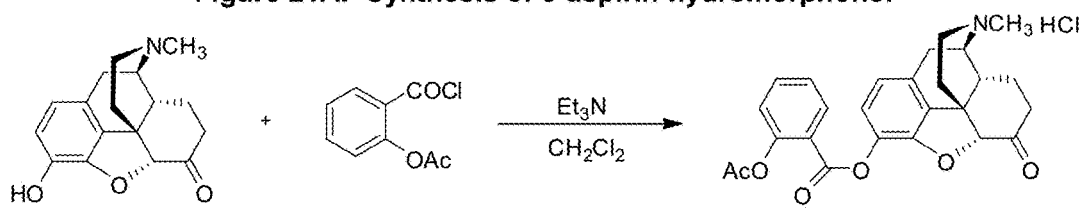
FIGS. 21A through 21D. Example synthetic schemes for the synthesis of some of the hydromorphone prodrugs of the present technology.

Synthesis of 3-aspirin-HM.HCl (FIG. 21A)

Triethylamine (0.42 mL, 3 mmol) was added to hydromorphone hydrochloride (0.322 g, 1 mmol) in dichloromethane (10 mL) followed by O-acetylsalicyloyl chloride (0.248 g, 1.25 mmol). The reaction was stirred at room temperature for 4 hours. The mixture was poured into ethyl acetate (100 mL) and washed with aqueous saturated NaHCO$_3$ (30 mL×3) and brine (30 mL). The organic layer was dried over anhydrous Na$_2$SO$_4$ and concentrated. The residue was purified by column chromatography (8% methanol in dichloromethane) to give 0.385 g of an amorphous solid, which was dissolved in methanol (6 mL) and then treated with 1 N HCl/MeOH (1.3 mL). The solvent was evaporated and TBME (6 mL) was added to the residue. The resulting white solid was collected and rinsed with TBME (1 mL×2). The yield was 0.395 g (81.6%).

Figure 21B:
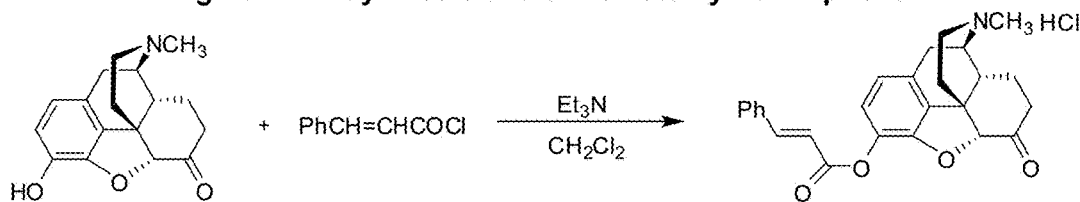

Synthesis of 3-cinnamate-HM.HCl (FIG. 21B)

The compound was synthesized using the same procedure as for 3-aspirin-HM, except the O-acetylsalicyloyl chloride was replaced by cinnamoyl chloride. The yield was 65.2%.

Figure 21C:
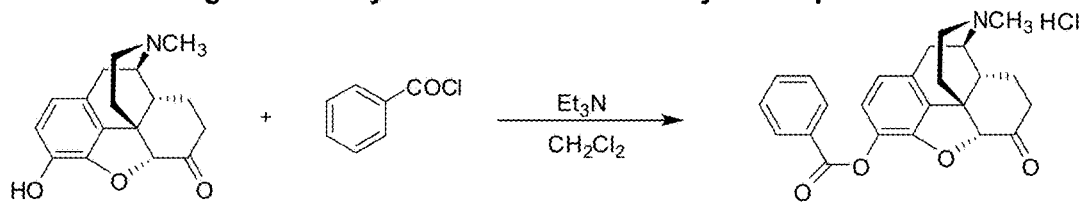

Synthesis of 3-benzoate-HM.HCl (FIG. 21C)

The compound was synthesized using the same procedure as for 3-aspirin-HM, except the O-acetylsalicyloyl chloride was replaced by benzoyl chloride. The yield was 58.9%.

Figure 21D:
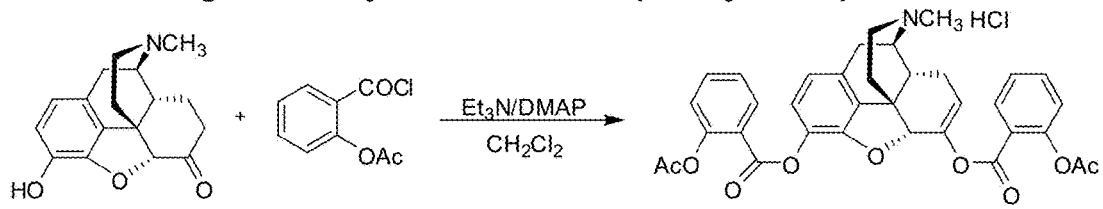
Figure 22:
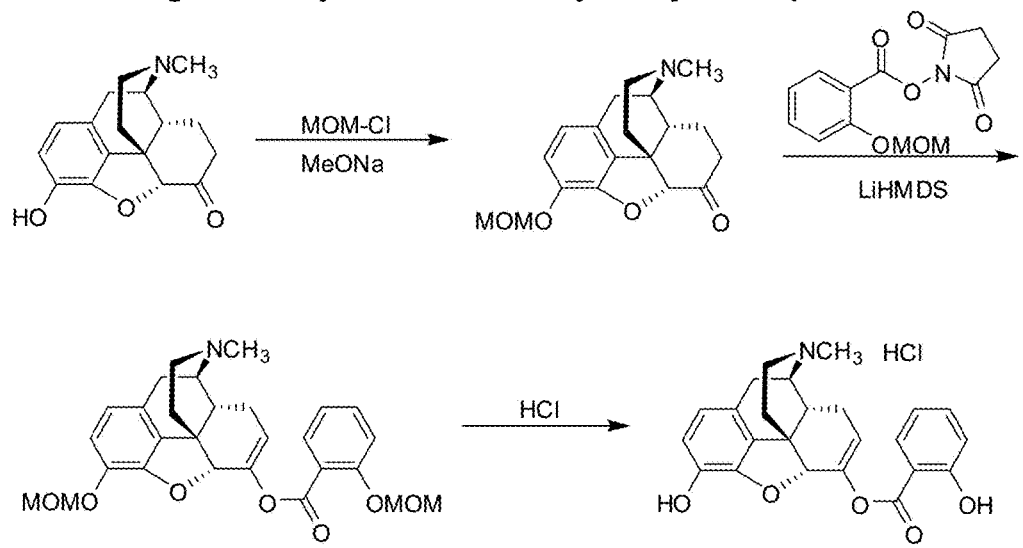
FIG. 22. Example synthetic scheme for the synthesis of some of the hydromorphone prodrugs of the present technology.

Synthesis of 3,6-di-aspirin-HM.HCl (FIG. 21D)

Triethylamine (0.70 mL, 5 mmol) was added to hydromorphone hydrochloride (0.322 g, 1 mmol) in dichloromethane (15 mL) followed by DMAP (48.9 mg, 0.4 mmol) and O-acetylsalicyloyl chloride (0.794 g, 4 mmol). The reaction was stirred at room temperature for 48 hours. The mixture was poured into ethyl acetate (100 mL) and washed with aqueous saturated NaHCO$_3$ (30 mL×3) and brine (30 mL). The organic layer was dried over anhydrous Na$_2$SO$_4$ and concentrated. The residue was purified by column chromatography (ethyl acetate and then 8% methanol in dichloromethane) and subsequently further purified by PTLC (8% methanol in dichloromethane). The desired fraction was concentrated and converted to its HCl salt by adding 1 N HCl (1 mL). The solvent was evaporated and to the residue was added ether (15 mL). The resulting solid was collected and rinsed with ether (2 mL×3). The yield was 0.203 g (31.4%).

Synthesis of 6-salicylate-HM.HCl (FIG. 21E)

Step 1 (3-MOM-HM)

0.5 M MeONa/MeOH (80 mL, 40 mmol) was added to hydromorphone hydrochloride (6.436 g, 20 mmol) in methanol (50 mL). The solvent was evaporated and the residue was coevaporated with toluene (25 mL×2). MOMCl (1.691 g, 21 mmol) in chloroform (5 mL) was added to the resulting solid in chloroform (100 mL) over 5 minutes while cooling in an ice-bath. The reaction was stirred at room temperature overnight. Solvents were evaporated and the resulting residue was purified by column (8% methanol in chloroform) yielding 5.77 g (87.5%) of an oil.

Step 2 (2-MOM-salicylic Acid Succinimidyl Ester)

2-MOM salicylic acid (3.2 g, 17.6 mmol) and N-hydroxy-succinimide (NHS, 2.23 g, 19.36 mmol) were dissolved in THF (anhydrous, 40 mL). DCC (3.99 g, 19.36 mmol) was added in one portion. The reaction was stirred overnight. Solids were filtered off. The filtrate was concentrated to dryness and the residue was recrystallized from methanol (10 mL). The resulting white solid was collected and rinsed with methanol (3 mL×2). The yield was 2.599 g (52.8%).

Step 3 (3-MOM-6-(2-MOM-salicylate)-HM)

1M LiHMDS/THF (3 mL, 3 mmol) was added to 3-MOM-protected hydromorphone (0.329 g, 1 mmol) in THF (anhydrous, 8 mL) over 5 minutes while cooling in an ice-bath. The mixture was then stirred for 20 minutes at room temperature. Upon cooling in an ice-bath, the 2-MOM-salicylic acid succinimidyl ester (0.838 g, 3 mmol) was added in one portion. The reaction was stirred for 6 hours. Saturated NH$_4$Cl (30 mL) was added to quench the reaction. The mixture was stirred for 30 minutes and extracted with ethyl acetate (100 mL). The acetate layer was washed with saturated NaHCO$_3$ (30 mL×2) and brine (30 mL), dried over anhydrous Na$_2$SO$_4$ and concentrated. The residue was purified by column (ethyl acetate and then 7% methanol in dichloromethane) yielding 100 mg of a syrup (20.2%).

Step 4 (6-Salicylate-HM.HCl)

The protected 3-MOM-6-(2-MOM-salicylate)-HM (100 mg) obtained in Step 3 was dissolved in methanol (1 mL). 1.25 N HCl/MeOH (3 mL) was added to the solution and the reaction was stirred for 3 hours. Solvents were evaporated and the residue was dissolved in methanol (0.5 mL). Ether (15 mL) was added and the resulting solid was collected by filtration and washed with ether (1 mL×3). The yield was 75 mg (83.7%).

In the present specification, use of the singular includes the plural except where specifically indicated.

The compositions, prodrugs, and methods described herein can be illustrated by the following embodiments enumerated in the numbered paragraphs that follow:

In one exemplar embodiment, the present technology is directed to a prodrug composition comprising at least one conjugate, the conjugate comprising at least one hydromorphone, and at least one aryl carboxylic acid. Further, the prodrug composition may also contain at least one hydromorphone and the at least one aryl carboxylic acid are chemically bonded to one another by reacting the carboxylic acid moiety of the aryl carboxylic acid with the C-6 enol tautomer of hydromorphone. Further, the prodrug composition may include or utilize at least one hydromorphone and the at least one aryl carboxylic acid are chemically bonded to one another by reacting the carboxylic acid moiety of the aryl carboxylic acid with the C-3 hydroxyl of hydromorphone. Moreover, such exemplar prodrug composition(s) may also contain or utilize at least one hydromorphone and the at least one aryl carboxylic acid are chemically bonded to one another by reacting the carboxylic acid moiety of one aryl carboxylic acid with the C-6 enol tautomer of hydromorphone and of one aryl carboxylic acid with the C-3 hydroxyl of hydromorphone. It should be appreciated that any of the above described exemplar embodiments/compositions can include or utilize at least one aryl carboxylic acid comprises a carboxylic group attached directly to at least one aryl moiety.

In at least one alternative exemplar embodiment of such prodrug composition(s), the at least one aryl carboxylic acid can be selected from a group consisting of, for example, benzoates and heteroaryl carboxylic acids. In other embodiments of the prodrug composition(s) the heteroaryl carboxylic acid is selected from the group consisting of pyridine, diazine and triazine. In some embodiments of the prodrug composition(s), the benzoate has the following general formula I:

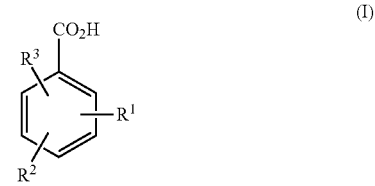

(I)

wherein $R^1$, $R^2$ and $R^3$ are independently selected from the group consisting of hydrogen, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, phosphonate.

In additional embodiments of the prodrug composition(s) the benzoate can be selected from the group consisting of, for example, aminobenzoates, hydroxybenzoates and aminohydroxybenzoates, mixtures thereof and derivatives thereof. Moreover, the prodrug composition(s) may contain or utilize an aminobenzoate that is selected from the group consisting of, for example, anthranilic acid, 3-aminobenzoic acid, 4,5-dimethylanthranilic acid, N-methylanthranilic acid, N-acetylanthranilic acid, fenamic acids, 2,4-diaminobenzoic acid (2,4-DABA), 2-acetylamino-4-aminobenzoic acid, 4-acetylamino-2-aminobenzoic acid and 2,4-diacetylaminobenzoic acid, mixtures thereof and derivatives thereof. Moreover, the prodrug composition(s) may contain or utilize an hydroxybenzoate that is selected from the group consisting of, for example, benzoic acid, salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m,p-thymotic acid, diflusinal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, and 3,4,5-trimethoxybenzoic acid, mixtures thereof and derivatives thereof. In still other alternative embodiments, the prodrug composition(s) may contain or utilize an aminohydroxybenzoate that is selected from the group consisting of, for example, 4-aminosalicylic acid, 3-hydroxyanthranilic acid, and 3-methoxyanthranilic acid, mixtures thereof and derivatives thereof.

In additional embodiments, the prodrug composition(s) may contain or utilize at least one aryl carboxylic acid that comprises a carboxylic group that is connected by a one-carbon linker to the aryl moiety.

In other embodiments, the prodrug composition(s) may contain or utilize at least one aryl carboxylic acid that is selected from the group consisting of branched phenylpropionic acids and phenylacetates, mixtures thereof and derivatives thereof. Moreover, the prodrug composition(s) may contain or utilize a phenylacetate that has the following general structure II:

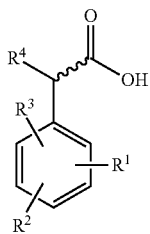

(II)

wherein $R^1$, $R^2$, $R^3$ and $R^4$ are independently selected from the group consisting of, for example, hydrogen, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, phosphonate. In additional embodiments, the prodrug composition(s) may contain or utilize a phenylacetate that is selected from the group consisting of, for example, phenylacetic acid (hydratropic acid), 2-hydroxyphenylacetic acid, 3-hydroxyphenylacetic acid, 4-hydroxyphenylacetic acid, homoprotocatechuic acid, homogentisic acid, 2,6-dihydroxyphenylacetic acid, homovanillic acid, homoisovanillic acid, homoveratric acid, atropic acid, d,l-tropic acid, diclofenac, d,l-mandelic acid, 3,4-dihydroxy-d,l-mandelic acid, vanillyl-d,l-mandelic acid, isovanillyl-d,l-mandelic acid, ibuprofen, fenoprofen, carprofen, flurbiprofen, ketoprofen and naproxen, mixtures thereof and derivatives thereof.

In some additional embodiments, the prodrug composition(s) may contain or utilize at least one aryl carboxylic acid that comprises a carboxylic group that is connected by a two-carbon linker to the aryl moiety. Additionally, the prodrug composition(s) may contain or utilize wherein at least one aryl carboxylic acid that is selected from the group consisting of benzylacetates and cinnamates, mixtures thereof and derivatives thereof. Further, the prodrug composition(s) may contain or utilize at least one aryl carboxylic acid that is selected from the group consisting of, for example, benzylacetates and cinnamates having the following general formula III or IV or combinations thereof:

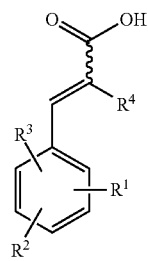

(III)

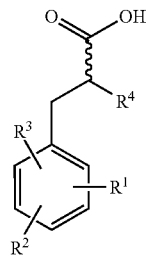

(IV)

wherein $R^1$, $R^2$, $R^3$ and $R^4$ are independently selected from the group consisting of hydrogen, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, phosphonate.

In additional embodiments, the prodrug composition(s) may contain or utilize a benzylacetate that is selected from the group consisting of, for example, benzylacetic acid, melilotic acid, 3-hydroxyphenylpropanoic acid, 4-hydroxyphenylpropanoic acid, 2,3-dihydroxyphenylpropanoic acid, d,l-phenyllactic acid, o,m,p-hydroxy-d,l-phenyllactic acid and phenylpyruvic acid, mixtures thereof and derivatives thereof. In alternative embodiments, the prodrug composition(s) may contain or utilize a cinnamate that is selected from the group consisting of, for example, cinnamic acid, o,m,p-coumaric acid, 2,3-dihydroxycinnamic acid, 2,6-dihydroxycinnamic acid, caffeic acid, ferulic acid, isoferulic acid, 5-hydroxyferulic acid, sinapic acid and 2-hydroxy-3-phenylpropenoic acid, mixtures thereof and derivatives thereof.

In some embodiments, the prodrug composition(s) may contain or utilize at least one aryl carboxylic acid that comprises a carboxylic group attached to an aryl moiety ring by an alkyl chain. In other embodiments, the prodrug composition(s) may contain or utilize an alkyl chain that comprises one carbon. In other embodiments, the prodrug composition(s) may contain or utilize an alkyl chain that comprises two carbons. In other embodiments, the prodrug composition(s) may contain or utilize at least one aryl carboxylic acid that comprises a carboxyl group attached to an aryl moiety by an alkenyl chain. In further embodiments, the prodrug composition(s) may contain or utilize an alkenyl chain that comprises two carbons. In other embodiments, the prodrug composition(s) may contain or utilize at least one aryl carboxylic acid that comprises one or more side chains. In additional embodiments, the prodrug composition(s) may contain or utilize at least one aryl carboxylic acid that comprises one or more functional groups. In alternative embodiments, the prodrug composition(s) may contain or utilize at least one aryl carboxylic acid that comprises at least one heteroaryl carboxylic acid.

In some embodiments, the prodrug composition(s) may contain or utilize a heteroaryl carboxylic acid that has, for example, one of the following general formulas V, VI, VII, VIII, IX, X, XI, XII, or XIII or combinations thereof:

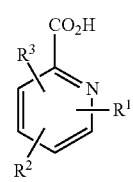

(V)

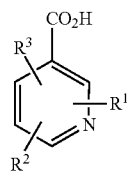

(VI)

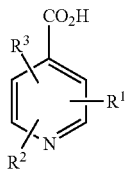

(VII)

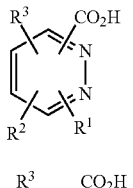

(VIII)

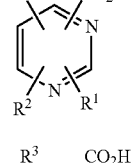

(IX)

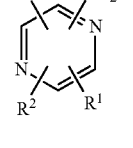

(X)

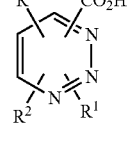

(XI)

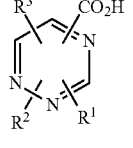

(XII)

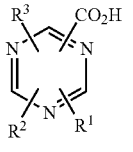

(XIII)

wherein $R^1$, $R^2$ and $R^3$ are independently selected from the group consisting of hydrogen, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, phosphonate.

In other embodiments, the prodrug composition(s) may contain or utilize a heteroaryl group that comprises one heteroatom. In further embodiments, the prodrug composition(s) may contain or utilize a heteroaryl carboxylic acid that is, for example, at least one pyridine or pyridine derivative. In additional embodiments, the prodrug composition(s) may contain or utilize a heteroaryl carboxylic acid that is selected from the group consisting of, for example, nicotinic acid (niacin), isonicotinic acid, picolinic acid, 3-hydroxypicolinic acid, 6-hydroxynicotinic acid, citrazinic acid, 2,6-dihydroxynicotinic acid, kynurenic acid, xanthurenic acid, 6-hydroxykynurenic acid, 8-methoxykynurenic acid, 7,8-dihydroxykynurenic acid and 7,8-dihydro-7,8-dihydroxykynurenic acid, mixtures thereof and derivatives thereof.

In other embodiments, the prodrug composition(s) may contain or utilize a heteroaryl group that comprises two heteroatoms. In further embodiments, the prodrug composition(s) may contain or utilize a heteroaryl carboxylic acid is, for example, at least one pyrazine, pyrimidine, pyridazine or derivatives thereof. In other embodiments, the prodrug composition(s) may contain or utilize a heteroaryl group that comprises three heteroatoms. In additional embodiments, the prodrug composition(s) may contain or utilize a heteroaryl carboxylic acid that is at least one 1,2,3-triazine, 1,2,4-triazine, 1,3,5-triazine or derivatives thereof. In other embodiments, the prodrug composition(s) may contain or utilize the at least one aryl carboxylic acid comprises a six-membered ring. Moreover, the prodrug composition(s) may contain or utilize a six-membered ring that comprises additional substituted or unsubstituted aromatic or aliphatic rings. In other embodiments, the prodrug composition(s) may contain or utilize at least one aryl carboxylic acid that comprises only one free carboxylic acid group. In further embodiments, the prodrug composition(s) may contain or utilize at least one aryl carboxylic acid that comprises, for example, between 1 to 4 substituents on the aryl ring.

In other embodiments, the prodrug composition(s) of the present technology may be in the form of a conjugate that is a neutral prodrug. In other embodiments, the prodrug composition(s) of the present technology may be in the form of a conjugate that is a free acid. In still other embodiments, the prodrug composition(s) of the present technology may be in the form of a conjugate that is a free base. In other embodiments, the prodrug composition(s) of the present technology may be in the form of a conjugate that is a pharmaceutically acceptable anionic or cationic salt form or salt mixtures thereof. In some embodiments, the prodrug composition(s) of the present technology may be in the form of a salt that is selected from the group consisting of, for example, acetate, l-aspartate, besylate, bicarbonate, carbonate, d-camsylate, l-camsylate, citrate, edisylate, formate, fumarate, gluconate, hydrobromide/bromide, hydrochloride/chloride, d-lactate, l-lactate, d,l-lactate, d,l-malate, l-malate, d-malate, mesylate, pamoate, phosphate, succinate, sulfate, bisulfate, d-tartrate, l-tartrate, d,l-tartrate, meso-tartrate, benzoate, gluceptate, d-glucuronate, hybenzate, isethionate, malonate, methylsufate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutarate, glycerophosphate, heptanoate (enanthate), hydroxybenzoate, hippurate, phenylpropionate, iodide, xinafoate, lactobionate, laurate, maleate, mandelate, methanesufonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminium, lithium, cholinate, lysinium, ammonium and tromethamine, mixtures thereof, and derivatives thereof.

In certain embodiments of the present technology, the prodrug composition(s) of the may be broken down in vivo releasing active hydromorphone, the aryl carboxylic acid, derivatives thereof and metabolites thereof. In other embodiments, the prodrug composition(s) of the present technology may be in the form of a prodrug that is administered orally and is hydrolyzed in vivo releasing hydromorphone from the prodrug. In additional embodiments, the prodrug composition(s) of the present technology may be in the form of a prodrug that exhibits no or limited pharmacological activity upon administration. In other embodiments, the prodrug composition(s) of the present technology may be in the form of a prodrug that releases hydromorphone in a manner that is similar to free or unmodified hydromorphone upon administration at equimolar dosages. In further embodiments, the prodrug composition(s) of the present technology may release hydromorphone into the systemic circulation in a decreased/controlled manner when the prodrug is administered via routes other than oral. In other embodiments, the prodrug composition(s) of the present technology may be in the form of a prodrug that releases hydromorphone in a controlled or sustained manner upon administration.

In certain embodiments of the present technology, the prodrug composition(s) of may be in the form of a prodrug that has no or decreased side effects compared to unmodified hydromorphone upon administration at equimolar dosages. In other embodiments, the prodrug composition(s) may be in the form of a prodrug that exhibits no or decreased side effects selected from, for example, dizziness, lightheadedness, drowsiness, nausea, vomiting, constipation, stomach pain, rash, difficulty urinating, difficulty breathing, neuroexcitatory effects or fainting.

In other embodiments of the present technology, the prodrug composition(s) do not result in high hydromorphone concentrations in the plasma or blood compared to unmodified hydromorphone upon administration at equimolar dosages by intravenous or intranasal routes. In further embodiments, the prodrug composition(s) do not cause or reduce euphoria or drug liking effects upon intranasal administration. In other embodiments, the prodrug composition(s) do not cause or reduces euphoria or drug liking effects upon intravenous administration. In alternative embodiments, the prodrug composition(s) do not result in a rapid hydromorphone concentration spike ($C_{max}$) in the blood or plasma upon oral administration. In additional embodiments, the prodrug composition(s) exhibit a delayed $T_{max}$ compared to unmodified hydromorphone when administered orally at equimolar dosages. In other embodiments, the prodrug composition(s) exhibit a lower $C_{max}$ value compared to unmodified hydromorphone when administered orally at equimolar dosages. In additional embodiments, the prodrug composition(s) exhibit increased relative bioavailability of hydromorphone compared to unmodified hydromorphone when administered orally at equimolar dosages. In further embodiments, the prodrug composition(s) exhibit a higher $C_{max}$ value compared to unmodified hydromorphone when administered orally at equimolar dosages. In alternative embodiments, the prodrug composition(s) a higher AUC value compared to unmodified hydromorphone when administered orally at equimolar dosages. In additional embodiments, the prodrug composition(s) exhibit higher $C_{max}$ and AUC values compared to unmodified hydromorphone when administered orally at equimolar dosages.

In other embodiments of the present technology, the prodrug composition(s) do not liberate hydromorphone when the composition is physically manipulated. In additional embodiments, the prodrug composition(s) exhibit resistance to certain chemical manipulations intended to liberate free hydromorphone.

In additional embodiments of the present technology, the prodrug composition(s) exhibit no or insignificant activity at µ-opioid receptors. In other embodiments, the prodrug composition(s) are not or limitedly subjected to enzymatic hydrolysis until it is absorbed in the gut. In additional embodiments, the prodrug composition(s) exhibit decreased conversion to hydromorphone-3-glucuronide (H3G) compared to unmodified hydromorphone when administered orally at equimolar dosages.

In other embodiments of the present technology, the prodrug composition(s) prevent or decrease opioid induced constipation (OIC) compared to unmodified hydromorphone when administered orally at equimolar dosages.

In certain embodiments of the present technology, the prodrug composition(s) additionally comprise, for example, ibuprofen, acetaminophen, or aspirin. In some embodiments of the present technology, the prodrug composition(s) contain or utilize a conjugate that is selected from the group consisting of, for example, 3-aspirin-hydromorphone, 3,6-di-aspirin-hydromorphone, 6-o-salicylate-hydromorphone, 3-cinnamate-hydromorphone, 6-naproxen-hydromorphone, 3-isoniacin-hydromorphone, 3-p-salicylic-hydromorphone, 3-fenamate-hydromorphone, 3-benzoate-hydromorphone, and 3,6-di-benzoate-hydromorphone.

In other embodiments of the present technology, the prodrug composition(s) are in an oral dosage form. In additional embodiments, the prodrug composition(s) are in an oral dosage form that is selected from the group consisting of, for example, tablet, capsule, caplet, troche, lozenge, powder, suspension, syrup, solution, softgel capsule, slurry, sublingual drops and oral thin film (OTF). In certain embodiments, the prodrug composition(s) are an oral dosage form that is a solid dosage form. In other embodiments, the prodrug composition(s) are in a solid dosage form and also contain at least one excipient. In further embodiments, the prodrug composition(s) contain an excipient that is selected from the group consisting of, for example, antiadherents, binders, coatings, disintegrants, fillers, flavors, colors, glidants, lubricants, preservatives, sorbents and sweeteners. In additional embodiments, the prodrug composition(s) are formulated into tablets, capsules, modified release capsules, softgel capsules, extended release tablets, controlled release capsules, suppositories, powders for injection, oral liquids, cough syrups, transdermal film, slurry or injections.

In other embodiments of the present technology, the prodrug composition(s) are in an oral dosage strength that is equimolar to from about 0.1 mg to about 200 mg of unmodified hydromorphone. In additional embodiments, the prodrug composition(s) are in an oral dosage strength that is equimolar to from about 1 mg to about 200 mg of unmodified hydromorphone. In other embodiments, the prodrug composition(s) are in an oral dosage strength that is equimolar to from about 2 mg to about 8 mg of unmodified hydromorphone. In further embodiments, the prodrug composition(s) are in an oral dosage strength that is equimolar to from about 8 mg to about 60 mg of unmodified hydromorphone. In additional embodiments, the prodrug composition(s) are in an oral dosage strength that is equimolar to from about 60 mg to about 200 mg of unmodified hydromorphone.

Other embodiments of the present technology are directed to methods of treating a patient in need of an analgesic effect by administering an effective amount of any of the prodrug composition(s) of the present technology. Additional embodiments of the present technology are directed to treating a patient in need of a cough suppressant by administering an effective amount of any of the prodrug composition(s) of the present technology. In additional embodiments, the present technology is directed to a method of treating a patient in need of therapy for narcotic or drug addiction by administering an effective amount of any of the prodrug composition(s) of the present technology. In certain methods of treatment of the present technology the prodrug composition(s) are in an oral dosage form. In other methods of treatment of the present technology the prodrug composition(s) are in an oral dosage form that is selected from, for example, a tablet, capsule, caplet, troche, lozenge, powder, suspension, syrup, solution, softgel capsule, slurry, sublingual drops and oral thin film (OTF). In additional methods of treatment of the present technology the prodrug composition(s) are in a solid dosage form. In other embodiments, the methods of treatment of the present technology comprise prodrug composition(s) in a solid dosage form that further comprises an excipient. In additional embodiments, the methods of treatment of the present technology comprise prodrug composition(s) in a solid dosage form that further comprises an excipient that is selected from the group consisting of, for example, antiadherents, binders, coatings, disintegrants, fillers, flavors, colors, glidants, lubricants, preservatives, sorbents and sweeteners.

In other embodiments, the methods of the present technology utilize prodrug composition(s) that are formulated into, for example, tablets, capsules, modified release capsules, softgel capsules, extended release tablets, controlled release capsules, suppositories, powders for injection, oral liquids, cough syrups, transdermal film, slurry or injections. In other embodiments, the methods of the present technology utilize prodrug composition(s) wherein the oral dosage strength is equimolar to from about 0.1 mg to about 200 mg of unmodified hydromorphone. In additional embodiments, the methods of the present technology utilize prodrug composition(s) wherein the oral dosage strength is equimolar to from about 2 mg to about 8 mg of unmodified hydromorphone. In further embodiments, the methods of the present technology utilize prodrug composition(s) wherein the oral dosage strength is equimolar to from about 8 mg to about 60 mg of unmodified hydromorphone. In other embodiments, the methods of the present technology utilize prodrug composition(s) wherein the oral dosage strength is equimolar to from about 60 mg to about 200 mg of unmodified hydromorphone.

Additional embodiments of the present technology are directed to methods of synthesizing any of the prodrug composition(s) of the present technology wherein the synthesis comprises the steps of chemically bonding at least one aryl carboxylic acid to at least one hydromorphone. In other embodiments, the methods of synthesizing any of the prodrug composition(s) of the present technology are directed to the synthesis of, for example, 3-aspirin-hydromorphone, 3,6-di-aspirin-hydromorphone, 6-salicylate-hydromorphone, 3-cinnamate-hydromorphone and 3-benzoate-hydromorphone.

Other embodiments of the present technology are directed to a pharmaceutical kit comprising a specified amount of individual doses of the prodrug composition(s) of the present technology in a package containing a pharmaceutically effective amount of at least one conjugate wherein the conjugate comprises at least one hydromorphone and at least one aryl carboxylic acid. In further embodiments, the kits of the present technology include a method of treating or preventing pain in a human or animal patient. In additional embodiments, the kits of the present technology are for treating a pediatric patient, an elderly patient and/or a normative patient. In further embodiments, the kits of the present technology include individual dosages of the prodrug composition(s) of the present technology comprising at least about 0.1 mg or higher of at least one conjugate of the present technology. In other embodiments, the kits of the present technology include individual dosages of the prodrug composition(s) of the present technology comprising at least about 1 mg, about 2.5 mg, about 5.0 mg, about 10 mg, about 20 mg, about 50 mg, about 100 mg, about 200 mg, about 500 mg, or higher of at least one conjugate of the present technology. In additional embodiments, the kits of the present technology include from about 1 to about 90, about 1 to about 60, or about 10 to about 30 individual doses of at least one prodrug composition(s) of the current technology.

The presently described technology is now described in such full, clear, concise, and exact terms as to enable any person skilled in the art to which it pertains, to practice the same. It is to be understood that the foregoing describes preferred embodiments of the technology and that modifications may be made therein without departing from the spirit or scope of the invention as set forth in the appended claims.

The invention claimed is:

1. A composition comprising a hydromorphone conjugate wherein the hydromorphone conjugate is 3-cinnamate-hydromorphone, a pharmaceutically acceptable salt thereof, or a combination thereof.

2. The composition of claim 1, where in the hydromorphone conjugate has the following structural formula

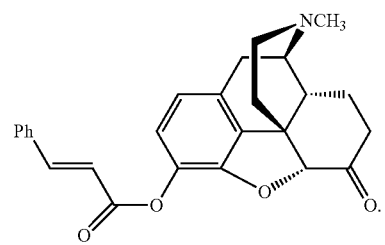

3. The composition of claim 1, wherein the hydromorphone conjugate and/or at least one pharmaceutically acceptable salt thereof is used to treat narcotic or opioid abuse; to prevent narcotic or opioid withdrawal; to treat moderate to severe pain; to reduce or prevent oral, intranasal or intravenous drug abuse; or to provide oral, intranasal, or parenteral drug abuse resistance.

4. The composition of claim 1, wherein the hydromorphone conjugate and/or at least one pharmaceutically acceptable salt thereof is provided in a dosage form selected from the group consisting of a tablet, a capsule, a caplet, a suppository, a troche, a lozenge, a powder, a solution, a film, a thin strip, a slurry, a suspension, a gel, a strip, a rectal film, a transdermal patch, a syrup, and an inhalation compound.

5. The composition of claim 1, wherein the composition is formulated for oral administration.

6. The composition of claim 5, wherein oral administration of the hydromorphone conjugate and/or at least one pharmaceutically acceptable salt thereof results in an improved rate of release over time when compared to unconjugated hydromorphone over the same time period.

7. The composition of claim 5, wherein oral administration of the hydromorphone conjugate and/or at least one pharmaceutically acceptable salt thereof results in less variability in the oral PK profile when compared to unconjugated hydromorphone.

8. The composition of claim 5, wherein oral administration of the hydromorphone conjugate and/or at least one pharmaceutically acceptable salt thereof results in reduced side effects when compared with unconjugated hydromorphone.

9. The composition of claim 8, wherein the reduced side effect is reduced opioid induced constipation.

10. The composition of claim 5, wherein oral administration of the hydromorphone conjugate and/or at least one pharmaceutically acceptable salt thereof provides a therapeutically bioequivalent AUC and/or a bioequivalent when compared to an equivalent molar amount of unconjugated hydromorphone.

11. The composition of claim 5, wherein oral administration of the hydromorphone conjugate and/or at least one pharmaceutically acceptable salt thereof provides a decreased overdose potential when compared to an equivalent molar amount of unconjugated hydromorphone.

12. The composition of claim 1, wherein the composition is formulated for intranasal or intravenous administration.

13. The composition of claim 12, wherein intranasal or intravenous administration of the at least one hydromorphone conjugate and/or at least one pharmaceutically acceptable salt thereof provides a lower AUC and/or Cmax when compared to an equivalent molar amount of unconjugated hydromorphone.

14. The composition of claim 1, wherein the hydromorphone conjugate and/or at least one pharmaceutically acceptable salt thereof provides an increased tamper resistance when compared to unconjugated hydromorphone.

15. The composition of claim 1, wherein the hydromorphone conjugate and/or pharmaceutically acceptable salt thereof is a prodrug.

16. The composition of claim 1, wherein the pharmaceutically acceptable salt of the hydromorphone conjugate is an anionic salt form, amphoteric salt form, zwitterionic salt form, cationic salt form, or salt form mixtures thereof.

17. The composition of claim 16, wherein the anionic salt form is selected from the group consisting of acetate, l-aspartate, besylate, bicarbonate, carbonate, d-camsylate, l-camsylate, citrate, edisylate, formate, fumarate, gluconate, hydrobromide/bromide, hydrochloride/chloride, d-lactate, l-lactate, d,l-lactate, d,l-malate, l-malate, d-malate, mesylate, pamoate, phosphate, succinate, sulfate, bisulfate, d-tartrate, l-tartrate, d,l-tartrate, meso-tartrate, benzoate, gluceptate, d-glucuronate, hybenzate, isethionate, malonate, methylsufate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutarate, glycerophosphate, heptanoate (enanthate), hydroxybenzoate, hippurate, phenylpropionate, iodide, xinafoate, lactobionate, laurate, maleate, mandelate, methanesufonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, and mixtures thereof.

18. The composition of claim 16, wherein the cationic salt form is selected from the group consisting of sodium, potassium, calcium, magnesium, zinc, aluminum, lithium, cholinate, lysinium, ammonium, tromethamine, and mixtures thereof.

19. A compound having the following structure

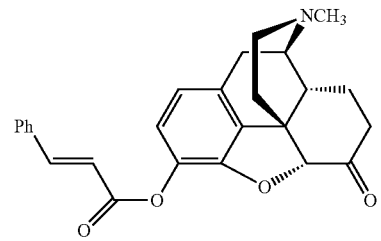

or a pharmaceutically acceptable salt thereof.

* * * * *